(12) United States Patent
Branchaud

(10) Patent No.: US 8,470,879 B2
(45) Date of Patent: Jun. 25, 2013

(54) FATTY ACID INHIBITORS

(75) Inventor: Bruce Branchaud, Eugene, OR (US)

(73) Assignee: Life Technologies Corporation, Carlsbad, CA (US)

( * ) Notice: Subject to any disclaimer, the term of this patent is extended or adjusted under 35 U.S.C. 154(b) by 0 days.

(21) Appl. No.: 12/917,847

(22) Filed: Nov. 2, 2010

(65) Prior Publication Data

US 2011/0105458 A1    May 5, 2011

Related U.S. Application Data

(60) Provisional application No. 61/257,315, filed on Nov. 2, 2009.

(51) Int. Cl.
*A61K 31/336* (2006.01)
*C07D 315/00* (2006.01)

(52) U.S. Cl.
USPC .......................................... 514/475; 549/200

(58) Field of Classification Search
USPC .......................................... 514/475; 549/200
See application file for complete search history.

(56) References Cited

U.S. PATENT DOCUMENTS

| | | | |
|---|---|---|---|
| 7,776,916 | B2 | 8/2010 | Freeman et al. |
| 2001/0023259 | A1 | 9/2001 | Slabas et al. |
| 2004/0225141 | A1 | 11/2004 | Rongione et al. |
| 2005/0143465 | A1 | 6/2005 | Pageat |
| 2009/0181937 | A1 | 7/2009 | Faucher et al. |
| 2009/0326070 | A1 | 12/2009 | Freeman et al. |

OTHER PUBLICATIONS

A compound CAS RN 607361-71-7 (2003).*
Walter L. Petty; "3-Nitro-3-methyl-1,2-epolybutane, a Novel α-Epoxide Synthesis"; J. Chem. Eng. Data, (1968) vol. 13, No. 4, 573.
Howard Newman and Robert B. Angier; "α-Nitro-epoxides, a new class of compounds", J. Chem. Soc. D, 1969, 369-370.
PCT/US2010/055100 International Preliminary Report on Patentability mailed Sep. 20, 2012.
Goodman & Gilman's "The Pharmacological Basis of Therapeutics" *Ninth Edition, Appendix II*, 1996, 1707-1711.
Adjei, Alex et al., "A Phase I Trial of the Farnesyl Transferase Inhibitor SCH66336: Evidence for Biological and Clinical Activity", *Cancer Research*, *60*, 2000, 1871-1877.
Banker, et al., "Modern Pharmaceutics", *Marcel Dekker, Inc.*, 1979,.
Blakemore, P. R., "The modified Julia olefination: alkene synthesis via the condensation of metallated heteroarylalkylsulfones with carbonyl compounds" *J. Chem. Soc., Perkin Trans.*, 2002, 2563-2585.
Boruwa, Joshodeep et al., "Catalytic Asymmetric Henry Reaction" *Tetrahedron: Asymmetry, 17*, 2006, 3315-3326.
De Meijere, Armin et al., "Metal-Catalyzed Cross-Coupling Reactions", *Wiley-VCH, Weinheim, XXII, ISBN-10: 3-527-30518-1; ISBN-13: 978-3-527-30518-6*, 2004.
Goodman & Gilman's "The Pharmacological Basis of Therapeutics", *Tenth Edition, Appendix II*, 2001, 1917-2023.
Karp, J. E. et al., "Clinical and biologic activity of the farnesyltransferase inhibitor R115777 in adults with refractory and relapsed acute leukemias: a phase 1 clinical-laboratory correlative trial", *Blood, 97(11)*, 2001, 3361-3369.
Kelly, Gregory S., "Conjugated Linoleic Acid: A Review", 2001, 367-382 *Altern Med Rev, vol. 6, No. 4*, 2001, 367-382.
Luzzio, Frederick, "The Henry reaction: recent examples", *Tetrahedron, 57*, 2001, 915-945.
March, J, "Advanced Organic Chemistry", 251-259 *McGraw Hill Book Company, New York*, 1977, 251-259.
Napolitano, Alessandra et al., "Reactions of Hydro(pero)xy Derivatives of Polyunsaturated Fatty Acids/Esters with Nitrite Ions under Acidic Conditions. Unusual Nitrosative Breakdown of Methyl 13-Hydro(pero)xyoctadeca-9,11-dienoate to a Novel 4-Nitro-2-oximinoalk-3-enal Product", *J. Org. Chem. vol. 67*, 2002, 1125-1132.
Rowe, R. C. et al., "Handbook of Pharmaceutical Excipients" *th ed.* 2006.
Woodcock, S. R. et al., "Synthesis of Nitrolipids. All Four Possible Nitrooleic Acids: (E)- and (Z)-, 9- and 10-Nitro-octadec-9-enoic No. 18, 2006, 3931-3934 Diastereomers of Acids", *Organic Letters; vol. 8, No. 18*, 2006, 3931-3934.

* cited by examiner

*Primary Examiner* — Yong Chu

(74) *Attorney, Agent, or Firm* — Life Technologies Corporation

(57) ABSTRACT

Fatty acid inhibitors, pharmaceutical compositions including fatty acid inhibitors, methods for using fatty acid inhibitors to treat a variety of diseases, and methods for preparing fatty acid inhibitors are provided herein.

3 Claims, No Drawings

FATTY ACID INHIBITORS

CROSS-REFERENCE TO RELATED APPLICATIONS

This application claims the benefit of priority to U.S. Provisional Patent Application No. 61/257,315 filed Nov. 2, 2009, which is herein incorporated by reference in its entirety.

GOVERNMENT INTERESTS

Not applicable

PARTIES TO A JOINT RESEARCH AGREEMENT

Not applicable

INCORPORATION BY REFERENCE OF MATERIAL SUBMITTED ON A COMPACT DISC

Not applicable

BACKGROUND

Not applicable

BRIEF SUMMARY OF THE INVENTION

Embodiments of the invention are generally directed to functionally-enhanced fatty acid inhibitors that form stable covalent bonds with thiol containing amino acids in the active site of proteins. In some embodiments, the covalent bond may be more stable than transient covalent bonds created during binding of the native substrate, and in other embodiments, the covalent bond may be irreversible. Binding of the functionally-enhanced fatty acid inhibitors described herein may inhibit activity of the binding protein by eliminating binding of the native substrate to the active site of the protein, and in some embodiments, binding of functionally-enhanced fatty acid inhibitors may irreversibly activate binding proteins by locking the binding protein in an active conformation inducing, for example, continuous activation of certain signaling pathways.

In various embodiments, the functionally-enhanced fatty acid inhibitors may be of Formulae I, Ia, II or IIa:

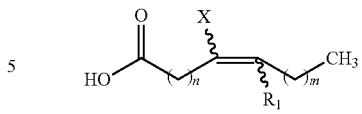

I

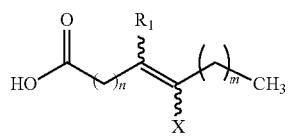

Ia

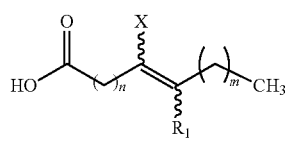

II

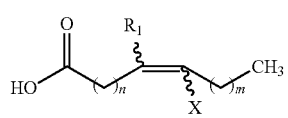

IIa where $R_1$ can be an electron withdrawing group such as any of those electron withdrawing groups described above, X can be a leaving group such as, but not limited to, leaving groups may include, but are not limited to, diazonium salts ($—N_2^+$), nonaflates ($R—OSO_2C_4F_9$), triflates ($—OSO_2CF_3$), fluorosulfonates ($—OSO_2F$), tosylates (—OTs), mesylates (—OMs) and similar compounds, halides, (—F, —Cl, —Br, —I), conjugate acid of alcohols ($—OH_2^+$), acyl chlorides (—R(O)Cl), conjugate acid of an ethers ($—OHR'^+$), nitrates ($—ONO_2$), phosphates ($—OPO(OH)_2$), tetraalkylammonium salts ($—NR'_3^+$), esters (—OC(O)R'), acid anhydrides (—C(O)OC(O)R'), ammonium salts($—NH_3^+$), phenoxides (—OAr), alcohols (—OH), carboxylic acids (—C(O)OH), ethers (—OR'), and esters (—C(O)OR') where each R' is independently hydrogen (—H) or $C_1$ to $C_6$ alkyl, alkeneyl, or alkynyl, and m and n can, independently, be 1-20; or Formulae IV, IVa, V, or Va:

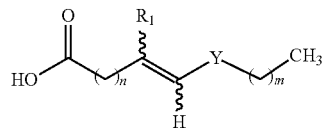

IV

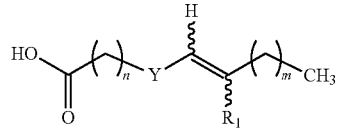

IVa

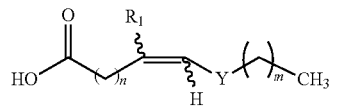

V

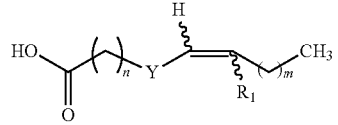

Va where $R_1$ is an electron withdrawing group, and Y is a leaving group within the main chain such as, for example, —O—, —NR"—, —S—, —SO—, $—SO^2—$, —POR"—, and the like, and m and n can each, individually, be 1-20; or Formulae VII, VIIa, VIII, or VIIIa:

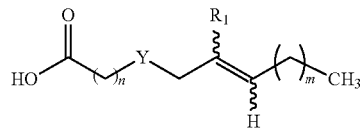

VII

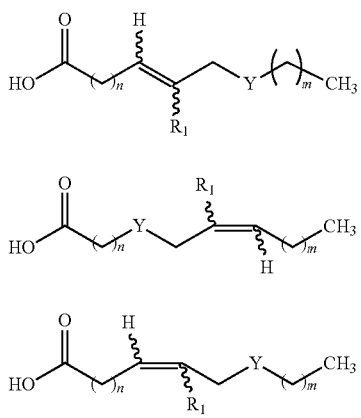

where $R_1$ is an electron withdrawing group, and Y is a leaving group within the main chain such as, for example, —O—, —NR″—, —S—, —SO—, —SO²—, —POR″—, and the like, and m and n can each, individually, be 1-20; or Formulae X, XI, XII, and XIIa

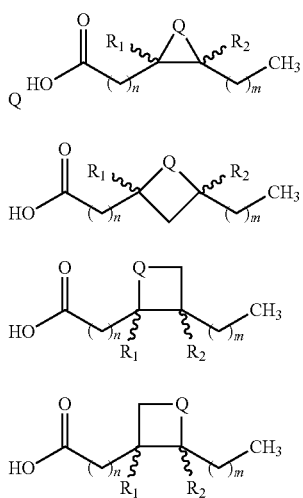

where one of $R_1$ or $R_2$ is an electron withdrawing group and the other is —H, Q can be any heteroatom, such as but not limited to —O—, —S—, —NR′″—, —CR′″₂—, and C=CR′″₂, where R′″ can be —H, $C_1$ to $C_6$ alkyl, alkeneyl, or alkynyl, aryl, and the like, and m and n can, independently, be 1-20; or Formulae XIII, XIV, XV, or XVa:

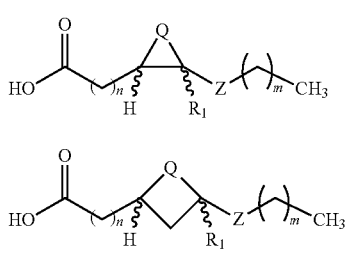

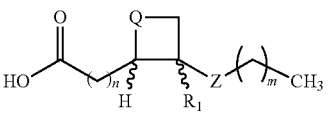

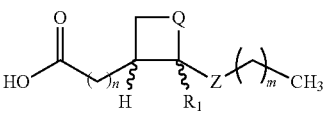

where $R_1$ is an electron withdrawing group, Q can be any heteroatom, such as, but not limited to, —O—, —S—, —NR′″—, —CR′″₂—, and C=CR′″₂, where R′″ can be —H, $C_1$ to $C_6$ alkyl, alkenenyl, or alkynyl, aryl, and the like, Z can be a ketone, ester, amide, thioester, and the like, and each m and n can, independently, be 1-20; or Formulae XVI, XVII, XVIII, or XVIIIa:

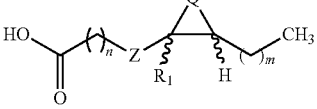

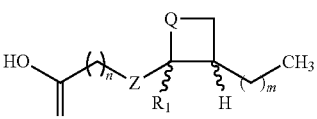

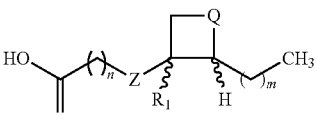

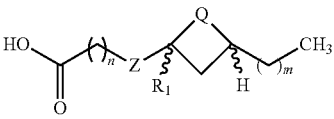

where $R_1$ is an electron withdrawing group, Q can be any heteroatom, such as, but not limited to, —O—, —S—, —NR′″—, —CR′″₂—, and C=CR′″₂, where R′l can be —H, $C_1$ to $C_6$ alkyl, alkenyl, or alkynyl, aryl, and the like, Z can be a ketone, ester, amide, thioester, and the like, and each m and n can, independently, be 1-20. In such embodiments, the electron withdrawing group may be, but are not limited to, aldehyde(—COH), acyl(—COR), carbonyl(—CO), carboxylic acid (—COON), ester(—COOR), halides (—Cl, —F, —Br, etc.), fluoromethyl (—$CF_n$), cyano(—CN), sulfonyl(—$SO_n$), sulfone(—$SO_2R$), sulfonic acid (—$SO_3H$), 1°, 2° and 3° ammonium (—$NR_3^+$), and nitro(—$NO_2$) where each R may, independently, be hydrogen, methyl, or $C_2$ to $C_6$ alkyl, alkenyl, or alkynyl. Other embodiments are directed to functionally-enhanced fatty acid inhibitors having a combination of thiol reactive groups such as those described above, or one or more additional double bonds and/or functional groups and/or heteroatoms positioned along the aliphatic chain of the fatty acid.

Still other embodiments are directed to pharmaceutical compositions including one or more functionally-enhanced fatty acid inhibitors such as those provided above and a pharmaceutically acceptable excipient or carrier, and methods for treating a disease that include administering such pharmaceutical compositions to an individual in need of treatment.

DESCRIPTION OF DRAWINGS

Not applicable

DETAILED DESCRIPTION

Before the present compositions and methods are described, it is to be understood that this invention is not limited to the particular processes, compositions, or methodologies described, as these may vary. It is also to be understood that the terminology used in the description is for the purpose of describing the particular versions or embodiments only, and is not intended to limit the scope of the present invention which will be limited only by the appended claims. Unless defined otherwise, all technical and scientific terms used herein have the same meaning as commonly understood by one of ordinary skill in the art. Although any methods and materials similar or equivalent to those described herein can be used in the practice or testing of embodiments of the present invention, the preferred methods, devices, and materials are now described. All publications mentioned herein are incorporated by reference in their entirety. Nothing herein is to be construed as an admission that the invention is not entitled to antedate such disclosure by virtue of prior invention.

It must also be noted that as used herein and in the appended claims, the singular forms "a," "an," and "the" include plural reference unless the context clearly dictates otherwise. Thus, for example, reference to a "cell" is a reference to one or more cells and equivalents thereof known to those skilled in the art, and so forth.

As used herein, the term "about" means plus or minus 10% of the numerical value of the number with which it is being used. Therefore, about 50% means in the range of 45%-55%.

"Administering" when used in conjunction with a therapeutic means to administer a therapeutic directly into or onto a target tissue or to administer a therapeutic to a patient, whereby the therapeutic positively impacts the tissue to which it is targeted. Thus, as used herein, the term "administering", when used in conjunction with a nitrated lipid can include, but is not limited to, providing a nitrated lipid to a subject systemically by, for example, intravenous injection, whereby the therapeutic reaches the target tissue. "Administering" a composition may be accomplished by, for example, injection, oral administration, topical administration, or by these methods in combination with other known techniques. Such combination techniques include heating, radiation, ultrasound and the use of delivery agents.

The term "animal" as used herein includes, but is not limited to, humans and non-human vertebrates such as wild, domestic and farm animals.

The term "improves" is used to convey that the present invention changes either the characteristics and/or the physical attributes of the tissue to which it is being provided, applied or administered. The term "improves" may also be used in conjunction with a diseased state such that when a diseased state is "improved" the symptoms or physical characteristics associated with the diseased state are diminished, reduced or eliminated.

The term "inhibiting" includes the administration of a compound of the present invention to prevent the onset of the symptoms, alleviating the symptoms, or eliminating the disease, condition or disorder.

By "pharmaceutically acceptable," it is meant the carrier, diluent or excipient must be compatible with the other ingredients of the formulation and not deleterious to the recipient thereof.

As used herein, the term "therapeutic" means an agent utilized to treat, combat, ameliorate, prevent or improve an unwanted condition or disease of a patient. In part, embodiments of the present invention are directed to the treatment of inflammation, obesity-related diseases, metabolic diseases, cardiovascular diseases, cerebrovascular and neurodegenerative diseases, cancer or the aberrant proliferation of cells.

A "therapeutically effective amount" or "effective amount" of a composition is a predetermined amount calculated to achieve the desired effect, i.e., to inhibit, block, or reverse the activation, migration, or proliferation of cells. The activity contemplated by the present methods includes both medical therapeutic and/or prophylactic treatment, as appropriate. The specific dose of a compound administered according to this invention to obtain therapeutic and/or prophylactic effects will, of course, be determined by the particular circumstances surrounding the case, including, for example, the compound administered, the route of administration, and the condition being treated. However, it will be understood that the effective amount administered will be determined by the physician in the light of the relevant circumstances including the condition to be treated, the choice of compound to be administered, and the chosen route of administration, and therefore, the above dosage ranges are not intended to limit the scope of the invention in any way. A therapeutically effective amount of compound of this invention is typically an amount such that when it is administered in a physiologically tolerable excipient composition, it is sufficient to achieve an effective systemic concentration or local concentration in the tissue.

The terms "treat," "treated," or "treating" as used herein refers to both therapeutic treatment and prophylactic or preventative measures, wherein the object is to prevent or slow down (lessen) an undesired physiological condition, disorder or disease, or to obtain beneficial or desired clinical results. For the purposes of this invention, beneficial or desired clinical results include, but are not limited to, alleviation of symptoms; diminishment of the extent of the condition, disorder or disease; stabilization (i.e., not worsening) of the state of the condition, disorder or disease; delay in onset or slowing of the progression of the condition, disorder or disease; amelioration of the condition, disorder or disease state; and remission (whether partial or total), whether detectable or undetectable, or enhancement or improvement of the condition, disorder or disease. Treatment includes eliciting a clinically significant response without excessive levels of side effects. Treatment also includes prolonging survival as compared to expected survival if not receiving treatment.

Generally speaking, the term "tissue" refers to any aggregation of similarly specialized cells which are united in the performance of a particular function.

Nitric oxide (NO) is an endogenously generated, lipophilic signaling molecule that has been implicated in the maintenance of vascular homeostasis, modulation of oxygen radical reactions, inflammatory cell function, post-translational protein modification and regulation of gene expression. In addition, nitric oxide-derived species display separate and unique pharmacological properties, specifically can mediate oxidation and nitration of biomolecules such as, for example, unsaturated fatty acids.

Various reactions yield products capable of concerted oxidation, nitrosation and nitration of target molecules. For example, nitric oxide may react with superoxide ($O_2^-$) to yield peroxynitrite ($ONOO^-$) and its conjugate acid, peroxynitritrous acid (ONOOH), the latter of which may undergo homolytic scission to form nitrogen dioxide ($.NO_2$) and hydroxyl radical (.OH). In some instances, biological conditions may favor the reaction of $ONOO^-$ with $CO_2$ which yields nitrosoperoxycarbonate ($ONOOCO_2^-$), which rapidly yields $.NO_2$ and carbonate ($.CO_3^-$) radicals via homolysis or rearrangement to $NO_3^-$ and $CO_2$. During inflammation, neutrophil myeloperoxidase and heme proteins such as myoglobin and cytochrome c catalyze $H_2O_2$-dependent oxidation of nitrite ($NO_2^-$) to $.NO_2$, resulting in biomolecule oxidation and nitration that is influenced by the spatial distribution of catalytic heme proteins. The reaction of .NO with $O_2$ can also produce products that can be substrates or reactants for nitrosation and nitration. For example, the small molecular radius, uncharged nature and lipophilicity of .NO and $O_2$ facilitate concentration of these species in biological membranes in a process referred to as the "molecular lens" effect. The increase in concentration induced by .NO and $O_2$ solvation in hydrophobic cell compartments accelerates the normally slow reaction of .NO with $O_2$ to yield $N_2O_3$ and $N_2O_4$. Finally, environmental sources also yield $.NO_2$ as a product of photochemical air pollution and tobacco smoke.

Nitration of fatty acids by $.NO_2$ can occur through several methods. For example, during both basal cell signaling and tissue inflammatory conditions, $.NO_2$ can react with membrane and lipoprotein lipids. In both in vivo and in vitro systems, $.NO_2$ has been shown to initiate radical chain autooxidation of polyunsaturated fatty acids via hydrogen abstraction from the bis-allylic carbon to form nitrous acid and a resonance-stabilized bis-allylic radical. Depending on the radical environment, the lipid radical species can react with molecular oxygen to form a peroxyl radical, which can react further to form lipid hydroperoxides then oxidized lipids. During inflammation or ischemia, when $O_2$ levels are lower, lipid radicals can react to an even greater extent with $.NO_2$ to generate multiple nitration products including singly nitrated, nitrohydroxy- and dinitro-fatty acid adducts. These products can be generated via hydrogen abstraction, direct addition of $.NO_2$ across the double bond, or both, and in some cases, such reactions may be followed by further reactions of the intermediate products that are formed. Hydrogen abstraction causes a rearrangement of the double bonds to form a conjugated diene; however, the addition of $.NO_2$ maintains a methylene-interrupted diene configuration to yield singly nitrated polyunsaturated fatty acids. This arrangement is similar to nitration products generated by the nitronium ion ($NO_2^+$), which can be produced by $ONOO^-$ reaction with heme proteins or via secondary products of $CO_2$ reaction with $ONOO^-$.

The reaction of polyunsaturated fatty acids with acidified nitrite ($HNO_2$) can generate a complex mixture of products similar to those formed by direct reaction with $.NO_2$, including the formation of singly nitrated products that maintain the bis-allylic bond arrangement. The acidification of $NO_2^-$ can create a labile species, $HNO_2$, which is in equilibrium with secondary products, including $N_2O_3$, .NO and $.NO_2$, all of which can participate in nitration reactions. The relevance of this pathway as a mechanism of fatty acid nitration is exemplified by physiological and pathological conditions wherein $NO_2^-$ is exposed to low pH (e.g., <pH 4.0). This may conceivably occur in the gastric compartment, following endosomal or phagolysosomal acidification or in tissues following-post ischemic reperfusion.

Nitrated linoleic acid ($LNO_2$) has been shown to display robust cell signaling activities that are generally anti-inflammatory in nature. Synthetic $LNO_2$ can inhibit human platelet function via cAMP-dependent mechanisms and inhibits neutrophil $O_2^-$ generation, calcium influx, elastase release, CD11b expression and degranulation via non-cAMP, non-cGMP-dependent mechanisms. $LNO_2$ may also induce vessel relaxation in part via cGMP-dependent mechanisms. In aggregate, these data, derived from a synthetic fatty acid infer that nitro derivatives of fatty acids ($NO_2$—FA) represent a novel class of lipid-derived signaling mediators. To date, a gap in the clinical detection and structural characterization of nitrated fatty acids has limited defining $NO_2$—FA derivatives as biologically-relevant lipid signaling mediators that converge .NO and oxygenated lipid signaling pathways.

As used herein a "duration-enhanced effectively-irreversible fatty acid inhibitors," "functionally-enhanced fatty acid inhibitors," or "fatty acid inhibitor" refers to a fatty acid having at least one electron withdrawing group covalently bound to a carbon of the saturated or unsaturated aliphatic chain of a fatty acid. Such fatty acid inhibitors may be substituted by any number of electron withdrawing groups at any number of positions on the hydrocarbon chain and such electron withdrawing groups may or may not be associated with a carbon-carbon double bond. Similarly, the fatty acid inhibitors described herein may include any number of double bonds which may or may not be associated with an electron withdrawing group.

Embodiments described herein are generally directed to activated unsaturated fatty acids and, in particular, "duration-enhanced effectively-irreversible fatty acid inhibitors," "functionally-enhanced fatty acid inhibitors," or "fatty acid inhibitor" that can irreversibly bind to proteins or for a more stable and, hence, long lasting bond of a protein than native fatty acids or activated fatty acid. Many proteins are known which bind to and react with fatty acids and activated fatty acids. Without wishing to be bound by theory, such proteins may bind to fatty acid inhibitors and form a more permanent, i.e., irreversible or more long lasting bond with the protein, and such irreversible or long lasting bonds may inhibit interactions with other fatty acids or activated fatty acid which may, for example, slow the catabolism of native substrates such as, fatty acids or activated fatty acids, inhibit further activation proteins that bind fatty acid inhibitors such as, for example, cell surface receptors, or permanently activate proteins that bind such proteins.

In general, the functionally-enhanced fatty acid inhibitors described herein include at least one an electron withdrawing group which may be associated with a double bond, a heteroatom, and/or a strained heterocycle. In some embodiments, functionally-enhanced fatty acid inhibitors may have one electron withdrawing group, and in other embodiments, functionally-enhanced fatty acid inhibitors may be substituted with multiple electron withdrawing groups at multiple positions along the hydrocarbon chain. In embodiments in which the electron withdrawing group is associated with a double bond, the electron withdrawing group may be positioned in either cis or trans configuration at the double bond or in either R or S absolute stereochemistry at an $sp^3$ chiral/stereogenic center. The fatty acid inhibitors may have an electron withdrawing group associated with a carbon-carbon double bond, a heteroatom, and/or a strained heterocycle positioned at any carbon along the aliphatic hydrocarbon chain between the carboxy terminal carbon to the terminal methyl (ω). For example, in some embodiments, the electron withdrawing group associated with a carbon-carbon double bond, a heteroatom, and/or a strained heterocycle may be positioned within about 1 carbon from the carboxy terminal carbon and within about 1 carbon from the terminal methyl, and in other embodiments, the electron withdrawing group associated with a carbon-carbon double bond, a heteroatom, and/or a strained heterocycle may be positioned within about 3 carbons of either the carboxy terminal carbon and/or the terminal methyl. In still other embodiments, the electron withdrawing group associated with a carbon-carbon double bond, a heteroatom, and/or a strained heterocycle may be positioned within 5 carbons of either of the carboxy terminal carbon and/or the methyl terminal carbon. While the length of the alkyl chain of functionally-enhanced fatty acid inhibitors of various embodiments may vary, the alkyl chains embodied above with regard to the position of the electron withdrawing group associated with a carbon-carbon double bond, a heteroatom, and/or a strained heterocycle may be from about 18 to about 24 carbons in length.

In certain embodiments, the electron withdrawing group may be positioned on a carbon directly attached to a double bond of the fatty acid inhibitor forming an "electron withdrawing vinyl" group. The electron withdrawing group of such vinyl groups may be on either side of the double bond. Thus, embodiments encompass regioisomers of any compound described herein. Fatty acids encompassed by embodiments of the invention may have one or more than one electron withdrawing vinyl groups at any carbon on the aliphatic hydrocarbon chain, and there are several ways that an unsaturated fatty acid can have one electron-withdrawing group. For example, in some embodiments, an activated oleic acid (ocatadecac-9-enoic acid) which is an 18 carbon, ω-6 fatty acid with one double bond (denoted "18:1") between the $6^{th}$ (C-13) and $7^{th}$ (C-12) carbons, may have an electron withdrawing group at either C-13 or C-12. In other exemplary embodiments, an activated linoleic acid (octadeac-9,12,-dienoic acid), which is an 18 carbon, ω-6 fatty acid with two double bonds (denoted "18:2") between the $6^{th}$ (C-13) and $7^{th}$ (C-12) carbons and the $9^{th}$ (C-10) and $10^{th}$ (C-9) carbons, may have an electron withdrawing group at C-9 or C-10 or C-12 or C-13. Similarly, other polyunsaturated fatty acids, with 3, 4, 5, 6 or more double bonds, can have one electron withdrawing at either position on any of the double bond carbons, including all possible permutations of positions and electron-withdrawing groups. As described above, the electron withdrawing group of such compounds may be positioned in either cis or trans configuration at the double bond or in either R or S absolute stereochemistry at an $sp^3$ chiral/stereogenic center.

In other embodiments, a mono or polyunsaturated fatty acid may have two or more electron-withdrawing groups, and there are several ways that an unsaturated fatty acid can have two or more electron-withdrawing groups. For example, in some embodiments, an activated oleic acid (ocatadecac-9-enoic acid) which is an 18 carbon, ω-6 fatty acid with one double bond (denoted "18:1") between the $6^{th}$ (C-13) and $7^{th}$ (C-12) carbons, may have an electron withdrawing group at both C-13 and C-12. In other exemplary embodiments, an activated linoleic acid (octadeac-9,12,-dienoic acid), which is an 18 carbon, ω-6 fatty acid with two double bonds (denoted "18:2") between the $6^{th}$ (C-13) and $7^{th}$ (C-12) carbons and the $9^{th}$ (C-10) and $10^{th}$ (C-9) carbons, may have an electron withdrawing group at any two of the positions C-9, C-10, C-12 or C-13, with the following possible permutations: C-9 and C-10, C-9 and C-12, C-9 and C-13, C-10 and C-12, C-10 and C-13, or C-12 and C-13. In other embodiments, a heteroatom or functional group located within the aliphatic chain may act as an electron withdrawing group when positioned within at least 2 carbons from a carbon-carbon double bond. Therefore, for example, a functionally-enhanced fatty acid inhibitor having a an in chain heteroatom such as, O, N, or S, or a functional group such as, a carbonyl, adjacent to a carbon-carbon double bond and an electron withdrawing groups such as a nitro group at another carbon-carbon double bond may be considered a functionally-enhanced fatty acid inhibitor having two electron withdrawing groups.

In analogy to the preceding descriptions of compounds with one electron-withdrawing group or two electron-withdrawing groups, it is also possible to have three, four, five or more electron withdrawing groups. Following the same logic above in the preceding descriptions of compounds with one electron-withdrawing group or two electron-withdrawing groups, polyunsaturated fatty acids, with 3, 4, 5, 6 or more double bonds, can have multiple electron withdrawing (three, four, five or more, as available positions for substitution permit) at any of the positions on any of the double bond carbons, including all possible permutations of positions and electron-withdrawing groups. Additionally, in any embodiments such as those described above, any number of non-electron-withdrawing groups may be covalently bound to carbons of the aliphatic chain of the fatty acid inhibitor. For example, in some embodiments, the fatty acid inhibitors of the invention may include one or more methyl, $C_2$-$C_6$ alkyl, alkenyl, or alkynyl or nitrogen-containing group, sulfur-containing group, phosphorus-containing group, halogen, or any other heteroatom-containing group covalently attached to one or more carbons of the aliphatic chain of a fatty acid inhibitor.

The term "electron-withdrawing group" is recognized in the art and denotes the tendency of a substituent to attract valence electrons from neighboring atoms, i.e., the substituent is electronegative with respect to neighboring atoms. A quantification of the level of electron-withdrawing capability is given by the Hammett sigma (σ) constant (see, e.g., J. March, Advanced Organic Chemistry, McGraw Hill Book Company, New York, (1977 edition) pp. 251-259). The Hammett constant values are generally negative for electron donating groups and positive for electron withdrawing groups. For example the Hammet constant for para substituted $NH_2$ (σ[P]) is about −0.7 and the σ[P] for a nitro group is about 0.8.

Embodiments of the invention encompass any known electron withdrawing group. For example, electron-withdrawing groups may include, but are not limited to, aldehyde(—COH), acyl(—COR), carbonyl(—CO), carboxylic acid (—COOH), ester(—COOR), halides(—Cl, —F, —Br, etc.), fluoromethyl(—$CF_n$), cyano(—CN), sulfonyl sulfone(—$SO_2R$), sulfonic acid (—$SO_3H$), 1°, 2° and 3° ammonium(—$NR_3^+$), and nitro(—$NO_2$) where each R may, independently, be hydrogen, methyl, or $C_2$ to $C_6$ alkyl, alkenyl, or alkynyl. In some embodiments, the electron withdrawing group may be a strong electron withdrawing group having a σ of at least about 0.2, and in certain embodiments, the electron withdrawing group may form a dipole. For example, in particular embodiments, the electron withdrawing group may be a nitro, ammonium or sulfonyl. In other embodiments, the fatty acid inhibitors of the invention may be additionally substituted by non-electron withdrawing groups or electron donating groups including, for example, alcohol (—OH), reverse ester (—OOCR), alkyl, alkenyl, alkynyl, 1° and 2° amines (—$NR_2$), nitrate (—$ONO_2$), nitrito (—ONO) and the like.

The fatty acids of embodiments may be any unsaturated and polyunsaturated fatty acid known in the art. The term "fatty acid" describes aliphatic monocarboxylic acids. Various embodiments include fatty acid inhibitors having an aliphatic hydrocarbon chain identical or similar to identified, naturally occurring fatty acids. For example, aliphatic hydrocarbon chains of known naturally occurring fatty acids are generally unbranched and contain an even number of from about 4 to about 24 carbons, and others include fatty acids having from 12 to 18 carbons in the aliphatic hydrocarbon chain. In still other embodiments, fatty acids may have greater than 24 carbons in the aliphatic hydrocarbon chain. Embodiments of the invention encompass such naturally occurring fatty acids as well as non-naturally occurring fatty acids, which may contain an odd number of carbons and/or a non-naturally occurring linker. Thus, some embodiments of the invention include fatty acids having an odd number of carbons of, for example, from 5 to 23 carbons, and in other embodiments, from 11 to 17 carbons. In yet other embodiments, the fatty acids of embodiments may have greater than 23 carbons.

The aliphatic hydrocarbon chain of fatty acids of various embodiments may be unsaturated or polyunsaturated. The term "unsaturated" refers to a fatty acid having a aliphatic hydrocarbon chain that includes at least one double bond and/or substituent. In contrast, a "saturated" hydrocarbon chain does not include any double bonds or substituents. Thus, each carbon of the hydrocarbon chain is 'saturated' and has the maximum number of hydrogens. "Polyunsaturated," generally, refers to fatty acids having hydrocarbon chains with more than one double bond. The double bonds of the unsaturated or polyunsaturated fatty acids of various embodiments may be at any location along the aliphatic hydrocarbon chain and may be in either cis or trans configuration. The term "cis," refers to a double bond in which carbons adjacent to the double bond are on the same side and the term "trans" refers to a double bond in which carbons adjacent to the double bond are on opposite sides. Typically "cis" is the same as Z, and "trans" is the same as E but sometimes the IUPAC rules for naming compounds will give the opposite of this, which is the typical case in nitroalkenes. For example, a nitroalkene can have the two carbon groups "cis" but the two groups that take priority for the naming of compounds (a nitro group on one carbon of the alkene and a carbon group on the other carbon of the alkene) are on opposite sides and thus are E. Therefore the nitroalkene analog of a "cis" double bond is actually an E nitroalkene. Similarly, the nitroalkene analog of a "trans" double bond is actually a Z nitroalkene. Without wishing to be bound by theory, double bonds in cis configuration along the carbon chain (cis carbon chain but E nitroalkene) may induce a bend in the hydrocarbon chain. Double bonds in "trans," configuration along the carbon chain (trans carbon chain but Z nitroalkene) may not cause the hydrocarbon chain to bend. Embodiments of the invention may include fatty acid inhibitors having double bonds in either cis or trans configuration, and encompass compositions that may include combinations of cis and trans containing fatty acid inhibitors and regioisomers of the fatty acid inhibitors.

Various embodiments of the invention include unsaturated or polyunsaturated fatty acids that may have a carbon-carbon double bond between any two carbons of the aliphatic chain of the fatty acid, and any number of carbon-carbon double bonds may be present in such polyunsaturated fatty acids. For example in some embodiments, polyunsaturated fatty acids may have 2, 3, 4, 5, 6 or more carbon-carbon double bonds. In such embodiments, each of the more than one carbon-carbon double bond may individually be in either cis or trans configuration. In some embodiments, at least one of the carbon-carbon double bonds of a polyunsaturated fatty acid may have an associated electron withdrawing group, and in other embodiments, more than one of the carbon-carbon double bonds of such polyunsaturated fatty acids may have an associated electron withdrawing group. Additionally, in such embodiments, the electron withdrawing group may be associated with either carbon of the carbon-carbon double bond or a carbon directly adjacent to either carbon of the carbon-carbon double bond. For example, in some embodiments, an electron withdrawing group may be attached to the alpha ($\alpha$) carbon of the carbon-carbon double bond, and in other embodiments, an electron withdrawing group may be associated with the beta ($\beta$) carbon of the carbon-carbon double bond. In still other embodiments, an electron withdrawing group may be associated with the gamma ($\gamma$) carbon, the carbon directly adjacent to, and attached to, a carbon-carbon double bond. In embodiments where a polyunsaturated fatty acid includes two or more carbon-carbon double bonds along the aliphatic chain and an electron withdrawing group is associated with any of the two or more carbon-carbon double bonds or each of the two or more of the carbon-carbon double bonds, each electron withdrawing group may be attached to any carbon associated with each individual carbon-carbon double bonds. For example, in some embodiments, an electron withdrawing group may be associated with each of the double bonds, with the electron group attached to either the ($\alpha$) carbon, the beta ($\beta$) carbon or the gamma ($\gamma$) carbon of each double bond. In other embodiments, some of the double bonds can have an attached electron withdrawing group and some of the double bonds will not have attached electron withdrawing groups, and those double bonds that do have attached electron withdrawing groups can have electron withdrawing groups attached at either the ($\alpha$) carbon, the beta ($\beta$) carbon or the gamma ($\gamma$) carbon of each double bond.

Many unsaturated and polyunsaturated fatty acids have been identified and are known to be naturally occurring. Such unsaturated or polyunsaturated naturally occurring fatty acids, generally, include an even number of carbons in their aliphatic hydrocarbon chain. For example, a naturally occurring unsaturated or polyunsaturated fatty acid may have, 4, 6, 8, 10, 12, 14, 16, 18, 20, 22 and so on carbons and may include omega ($\omega$)-3, $\omega$-5, $\omega$-6, $\omega$-7, $\omega$-9 fatty acids and the like. Any such fatty acid may be useful in embodiments of the invention. The symbol '$\omega$' is used to refer to the terminal methyl carbon of the aliphatic hydrocarbon chain. The placement of the double bond of the $\omega$-X fatty acid is the carbon-carbon bond X number of carbons from the $\omega$ carbon. For example, an $\omega$-6 fatty acid has a double bond between the $6^{th}$ and $7^{th}$ carbons counting backward from the $\omega$ carbon and an $\omega$-3 fatty acid has a double bond between the $3^{rd}$ and $4^{th}$ carbons counting backward from the $\omega$ carbon. Various embodiments of the invention include nitrated $\omega$-3 fatty acids, including, but not limited to, linolenic acid, alpha-linolenic acid, eicosapentanoic acid, docosapentaenoic acid, docosahexanoic acid and stearidonic acid; nitrated $\omega$-5 fatty acids including, but not limited to, myristoleic acid; nitrated $\omega$-6 fatty acids including, but not limited to, linoleic acid, gamma-linoleic acid, dihomo-gamma-linoleic acid and arachidonic acid; nitrated $\omega$-7 fatty acids including, but not limited to, palmitoleic acid; and nitrated $\omega$-9 fatty acids including, but not limited to, oleic acid and erucic acid. Of course, the fatty acids of the invention may also be referred to using IUPAC nomenclature in which the placement of the double bond is determined by counting from the carbon of the carboxylic acid, and 'C—X' denotes the carbon in aliphatic hydrocarbons using IUPAC nomenclature wherein X is the number of the carbon counting from the carboxylic acid. Embodiments of the invention also include synthetic equivalents to naturally occurring fatty acids and derivatives thereof.

Other embodiments of the invention include unsaturated or polyunsaturated non-naturally occurring fatty acids which may have an odd number of carbons such as, for example, 5, 7, 9, 11, 13, 15, 17, 19, 20, 21 and so on. As in naturally occurring fatty acids, the one or more double bonds associated with non-naturally occurring fatty acids may be at any position along the aliphatic hydrocarbon chain, and the double bonds may be in either cis or trans configuration. In yet other embodiments, the non-naturally occurring fatty acids may include one or more linker groups, which interrupt the aliphatic hydrocarbon chain. For example, in some embodiments, fatty acid inhibitors may have one or more non-carbon-carbon linkage such as, for example, ester, ether, vinyl ether, amino, imine and the like at any position within the aliphatic hydrocarbon chain.

Unsaturated and polyunsaturated fatty acids, whether naturally or non-naturally occurring, may be further referred to base on their degree of unsaturatation. The degree of unsaturation generally refers to the number of pairs of hydrogen atoms less than the number of hydrogen on a fully saturated fatty acid. Therefore, for example, fully saturated fatty acid has a degree of unsaturation of 0 whereas a fatty acid having degree of saturation of 1 has 2 less hydrogen atoms associated with the aliphatic chain of the fatty acid and a fatty acid having a degree of saturation of 2 has 4 less hydrogen atoms than its fully saturated counterpart. In most cases, an increase in the degree of unsaturation may indicate the presence of a double bond on the aliphatic chain; however, an increase in the degree of unsaturation may also indicate the presence of a ring structure that incorporates a portion of the aliphatic chain. For example, the functionally-enhanced fatty acid inhibitors described under Group IV below may be considered to have a degree of unsaturation of 1 if the strained heterocycle is the only moiety found on the aliphatic chain, of a degree of unsaturation of greater than one if additional heterocycles, double bonds, activated double bonds having associated electron withdrawing groups are also present on the aliphatic chain.

The fatty acids of various embodiments may also be branched at one or more location along the hydrocarbon chain, and in some embodiments, each branch may include an aliphatic hydrocarbon chain of from 1 to 24 carbons, 2 to 20 carbons or 4 to 18 carbons wherein each branch may have an even or odd number of carbons. The degree of branching may vary among embodiments, and in some embodiments, a functionally-enhanced fatty acid inhibitor may include from 0 to 6 branches along the aliphatic chain of the fatty acid. In other embodiments, one or more branch of a branched chain may have additional branches. In such embodiments, each branch may include one or more double bonds, activated double bonds having an associated electron withdrawing group, heteroatom, cyclic group, or heterocycle. For example in some embodiments, one branch or the main aliphatic chain may include such structures, and in other branches two or more branches or one or more branches and the main chain may include such structures.

In particular embodiments, an unsaturated fatty acid having at least one electron withdrawing group may be a conjugated fatty acid. In such embodiments, two carbon-carbon double bonds in an aliphatic chain are adjacent to one another such that there is no methylene group between them. Such conjugated compounds are commonly called 1,3-dienes, or conjugated fatty acids. Such 1,3-dienes may include one or more electron withdrawing groups at any of 6 positions, at the 1, 2, 3, and/or 4 positions of the 1,3-dienes and at the two carbons adjacent to the diene (at the 0 and 5 positions, in relation to the 1, 2, 3, 4 method of identifying carbons in a 1,3-diene). For example, one associated electron withdrawing group may be attached to any of the 6 positions identified above, that is to either the 1, 2, 3, or 4 positions on the diene or to either of the carbons adjacent to the 1,3-diene (at the 0 or 5 positions, as described above). In additional embodiments, two associated electron withdrawing groups could be attached to any two of the six possible positions, three associated electron withdrawing groups could be attached to any two of the six possible positions, four associated electron withdrawing groups could be attached to any two of the six possible positions, five associated electron withdrawing groups could be attached to any two of the six possible positions, and six associated electron withdrawing groups could be attached to any two of the six possible positions. In summary, any configuration of electron withdrawing groups attached to any of the six positions described above in a 1,3-diene are encompassed by embodiments of the invention.

In certain embodiments, the fatty acid inhibitors of the invention may undergo an isomerization following preparation such that either the cis/trans configuration of the double bond, the location of the double bond in the carbon chain, or both, may change. For example, in some embodiments, a fatty acid inhibitor may be prepared with a carbon-carbon double bond of having an electron withdrawing group attached to a gamma carbon of a carbon-carbon double bond. Following preparation, the carbon-carbon double bond may undergo an isomerization such that the electron withdrawing group is now conjugated with the carbon-carbon double bond after isomerization. Such isomerizations may occur spontaneously at any time following preparation, and may result in a composition which may have initially been prepared as including a single species of fatty acid inhibitor that subsequently includes a combination of isomers of the first-prepared fatty acid inhibitor originally produced. In other embodiments, a fatty acid inhibitor may be prepared having an electron withdrawing group attached to a gamma carbon of a carbon-carbon double bond, and this carbon-carbon double bond may undergo an isomerization following administration such that a fatty acid inhibitor is produced having the electron withdrawing group is conjugated with the carbon-carbon double bond.

Group I

In some embodiments, functionally-enhanced fatty acid inhibitors may be configured as described above may further include a second functional associated with the carbon-carbon double bond and positioned at the carbon adjacent to the electron withdrawing group, i.e., the beta position, such that both carbons of the carbon-carbon double bond are conjugated. In such embodiments, the second functional group may act as a "leaving group" during binding thereby allowing a thiol containing amino acid to form a covalent bond with the carbon atom conjugated to the second functional group. Embodiments are not limited by the type of leaving groups. For example, in various embodiments, leaving groups may include, but are not limited to, diazonium salts ($.N_2^+$), nonaflates ($R-OSO_2C_4F_9$), triflates($-OSO_2CF_3$), fluorosulfonates($-OSO_2F$), tosylates($-OTs$), mesylates($-OMs$) and similar compounds, halides, ($-F, -Cl, -Br, -I$), conjugate acid of alcohols ($-OH_2^+$), acyl chlorides($-R(O)Cl$), conjugate acid of an ethers($-OHR'^+$), nitrates($-ONO_2$), phosphates($-OPO(OH)_2$), tetraalkylammonium salts ($-NR'_3^+$), esters($-OC(O)R'$), acid anhydrides($-C(O)OC$ (O)R'), ammonium salts(—NH$_3^+$), phenoxides(—OAr), alcohols(—OH), carboxylic acids (—C(O)OH), ethers(—OR'), and esters (—C(O)OR') where each R' is independently hydrogen (—H) or lower alkyl.

Some embodiments include functionally-enhanced fatty acid inhibitors of Formulae I, Ia, II, and IIa:

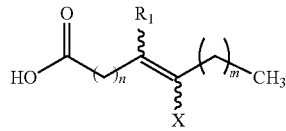

I

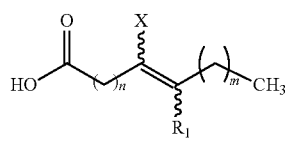

Ia

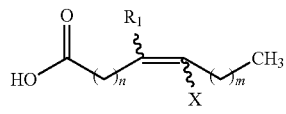

II

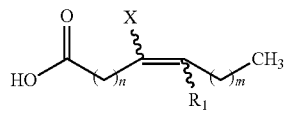

IIa where $R_1$ can be an electron withdrawing group such as any of those electron withdrawing groups described above, X can be any leaving group, and m and n can, independently, be 1-20. In other embodiments, such compounds may include one or more double bonds flanking the electron withdrawing group containing carbon-carbon double bond. Some embodiments include compounds of general Formulae III and IIIa:

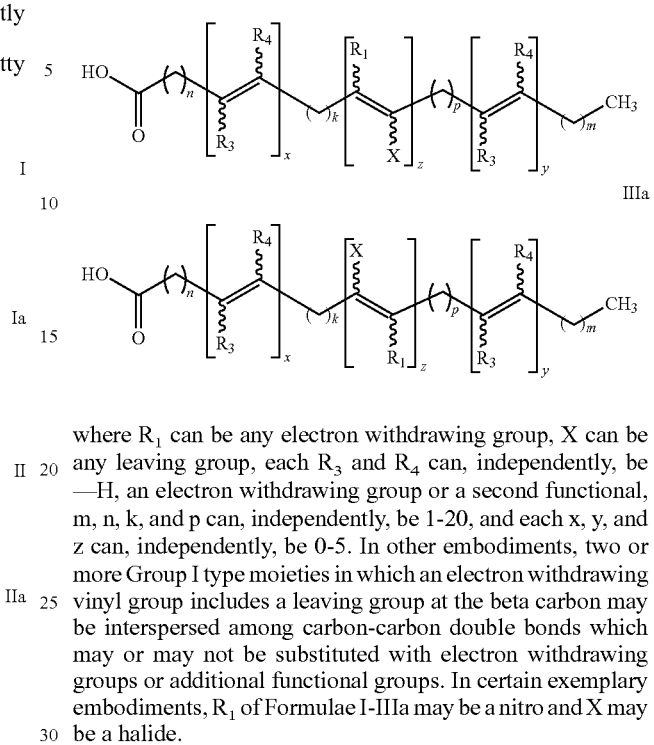

where $R_1$ can be any electron withdrawing group, X can be any leaving group, each $R_3$ and $R_4$ can, independently, be —H, an electron withdrawing group or a second functional, m, n, k, and p can, independently, be 1-20, and each x, y, and z can, independently, be 0-5. In other embodiments, two or more Group I type moieties in which an electron withdrawing vinyl group includes a leaving group at the beta carbon may be interspersed among carbon-carbon double bonds which may or may not be substituted with electron withdrawing groups or additional functional groups. In certain exemplary embodiments, $R_1$ of Formulae I-IIIa may be a nitro and X may be a halide.

Without wishing to be bound by theory, Group I functionally-enhanced fatty acid inhibitors having at least one double bond with a conjugated electron withdrawing group and a conjugated leaving group may interact with a active protein to form a reversible but stable covalent bond between the carbon-carbon double bond and a thiol containing amino acid in the active site of the protein as illustrated in Mechanism I:

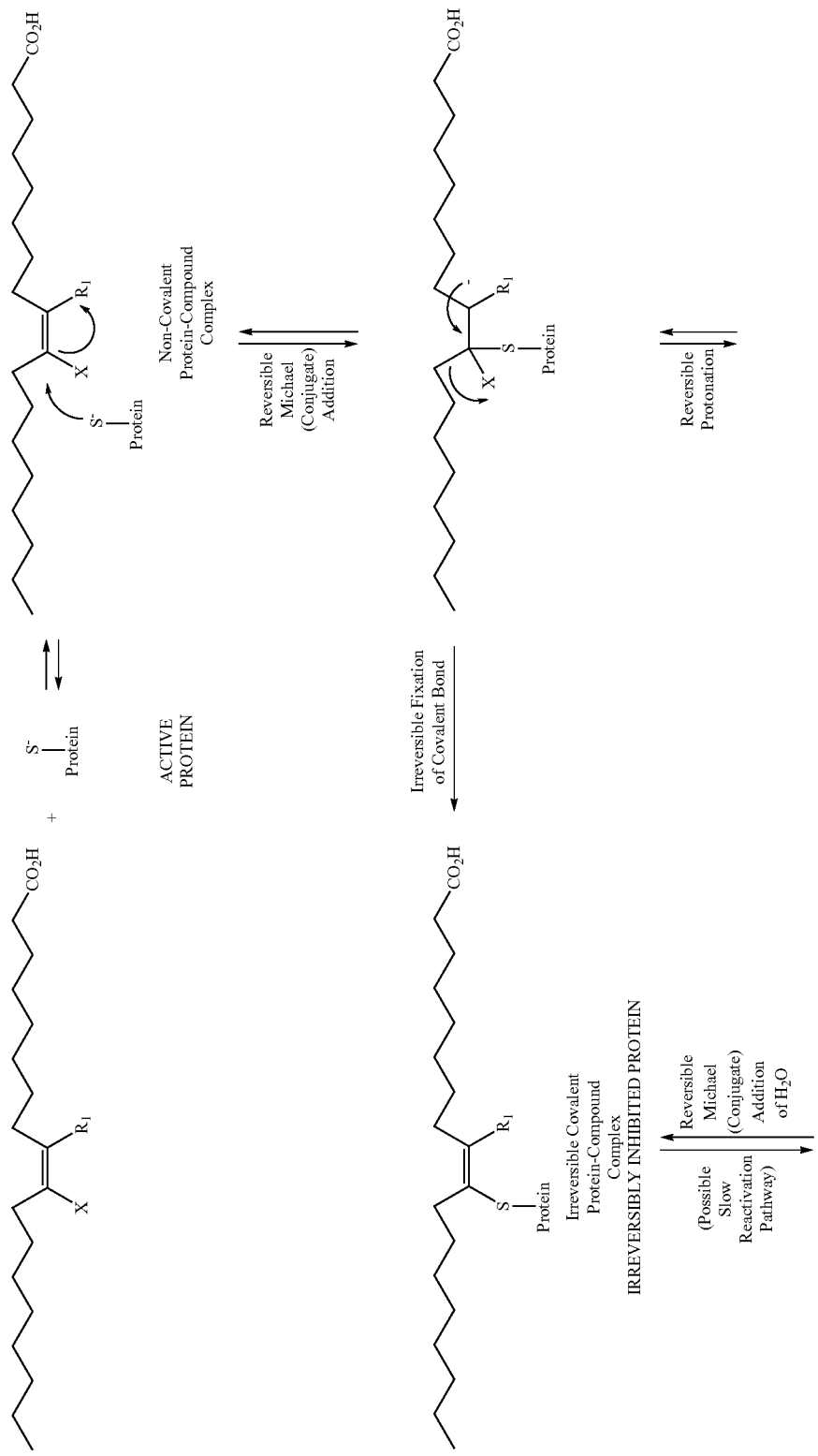

-continued
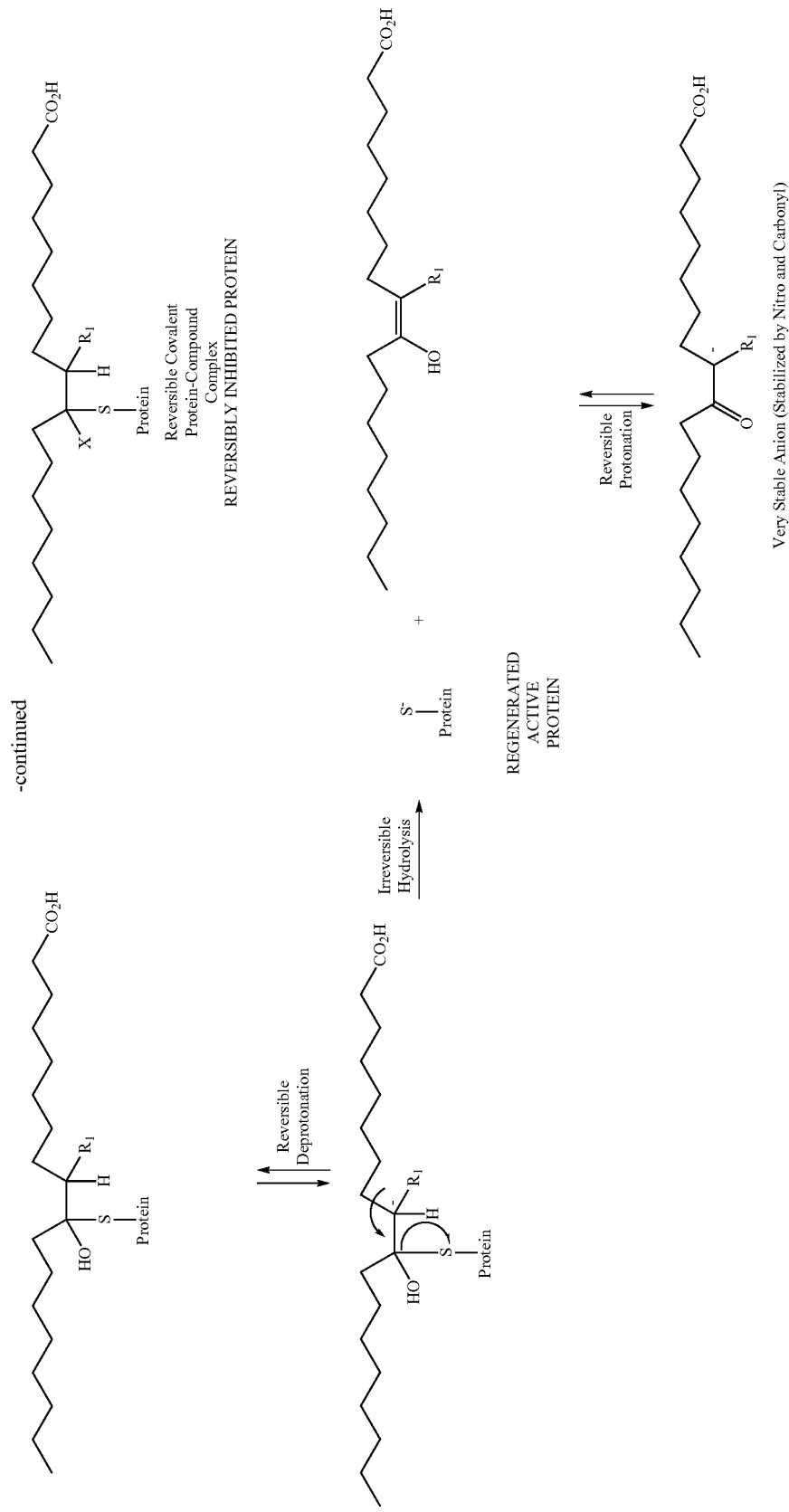

As indicated in Mechanism I once bound, the functionally-enhanced fatty acid inhibitors having a leaving group in the beta position are capable of undergoing may undergo a Michael addition with a thiol containing amino acid in the active site of the binding protein producing a covalent bond between the thiol and the beta carbon of the double bond. In some embodiments, the resulting protein-fatty acid inhibitor complex may undergo a reversible protonation which allows for the formation of a slowly reversible covalent bond with the thiol containing amino acid. While this interaction is not necessarily permanent, it may be less passive than the interaction of a functionally-enhanced fatty acid inhibitors that does not include a leaving group at the beta position. Group I functionally-enhanced fatty acid inhibitors may also undergo a fixation of the covalent bond in which the leaving group dissociates from the fatty acid inhibitor and the carbon-carbon double bond reforms with the thiol of the active protein replacing the leaving group. In such embodiments, the covalent bond between the thiol and the functionally-enhanced fatty acid inhibitor may be essentially irreversible and may permanently inhibit the activity of the binding protein. However, slow reversal of the covalent bond is possible in the presence of water, which may create a sub species that is susceptible to deprotonation and hydrolysis, which may reactivate the binding protein. Such reversal may be dependent upon the arrangement of the active site of the protein and, for example, the accessibility water in the active site, which may depend on the physical environment of the protein and/or activity at other active sites on the protein. Therefore, in some embodiments, Group I fatty acid inhibitors may either reduce the activity of binding proteins without permanently inhibiting binding proteins by occupying the active of such proteins precluding binding of other substrates or completely inhibit or "turn off" activity of the binding protein by forming a permanent interaction with the active site which completely precludes binding and catalysis of other substrates. In other embodiments, Group I functionally-enhanced fatty acid inhibitors may increase activation or permanently activate, permanently "turn on," a binding protein by occupying a binding site which, for example, causes a conformational change in the binding protein that activates a secondary active site.

Group II

In other embodiments, a leaving group may be provided in the main chain of the functionally-enhanced fatty acid inhibitors at replacing a carbon directly adjacent to a carbon of the carbon-carbon double bond that does not include an electron withdrawing group. For example, embodiments include functionally-enhanced fatty acid inhibitors of Formulae IV, IVa, V, and Va:

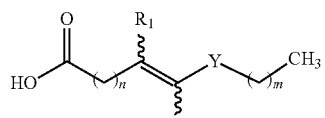

IV

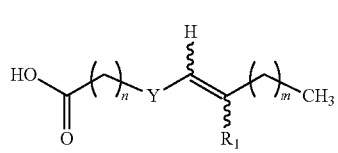

IVa

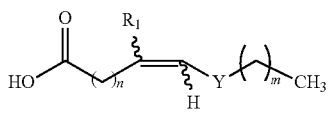

V

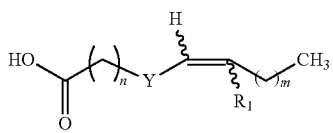

Va where $R_1$ is an electron withdrawing group, and Y is a leaving group within the main chain such as, for example, —O—, —NR"—, —S—, —SO—, —SO$^2$—, —POR"—, and the like, and m and n are each individually 1-20. In other embodiments, such compounds may include one or more double bonds flanking the electron withdrawing group containing carbon-carbon double bond. Some embodiments include compounds of general Formulae VI and VIa:

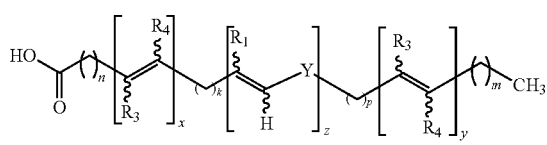

VI

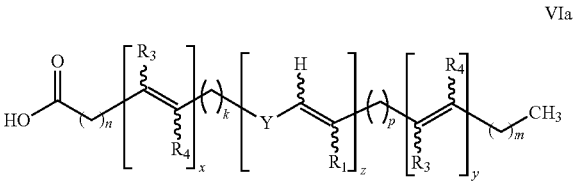

VIa where $R_1$ is an electron withdrawing group, and Y is a leaving group within the main chain, each $R_3$ and $R_4$ can, independently, be —H, an electron withdrawing group or a second functional group, m, n, k, and p can, independently; be 1-20, and each x, y, and z can independently be 0-5. In additional embodiments, fatty acid inhibitors such as those illustrated in Formulae VI and VIa may have additional heteroatoms located anywhere along the aliphatic chain, and in some embodiments, these heteroatoms may be associated with a carbon-carbon double bonds including an electron withdrawing group to create a fatty acid inhibitor with two or more carbon-carbon double bonds as illustrated in Formulae IV, IVa, V, and Va. In other embodiments, two or more Group II type moieties having electron withdrawing vinyl groups associated with a heteroatom at the gamma position on the aliphatic chain may be interspersed among additional carbon-carbon double bonds which may or may not have associated functional groups or additional functional groups. In certain exemplary embodiments, $R_1$ may be a nitro and Y may be sulfur.

Without wishing to be bound by theory, Group II functionally-enhanced fatty acid inhibitors may form a slowly reversible covalent bond with thiol containing amino acids in the active site of a binding protein. Formation of this slowly reversible covalent bond may provide permanent or long term inhibition of action of the protein or permanent or long term activation of the protein similar to that described under Group I. The proposed mechanism of action is illustrated in Mechanism II:

23

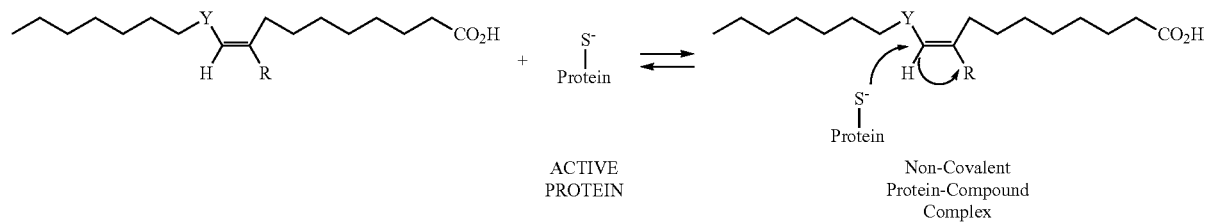

ACTIVE PROTEIN

Non-Covalent Protein-Compound Complex

24

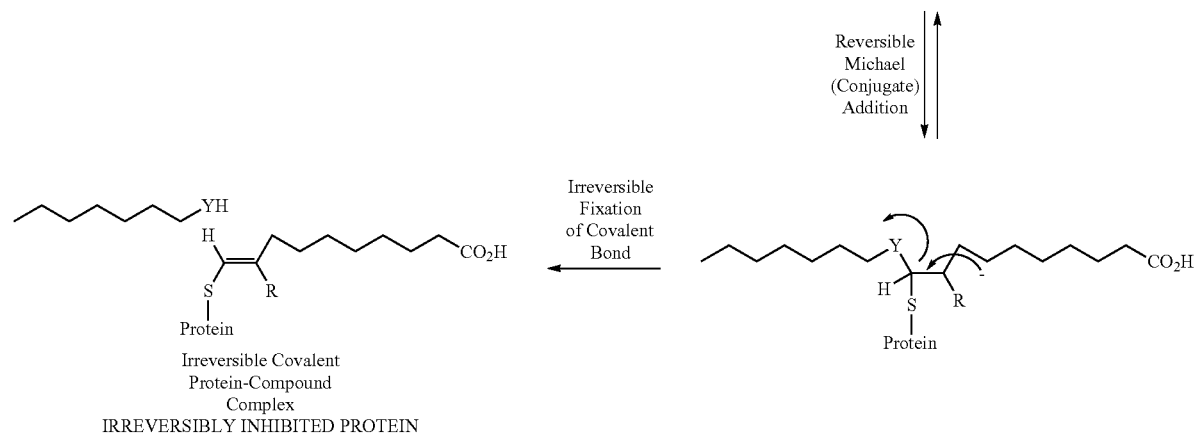

Reversible Michael (Conjugate) Addition

Irreversible Fixation of Covalent Bond

Irreversible Covalent Protein-Compound Complex
IRREVERSIBLY INHIBITED PROTEIN

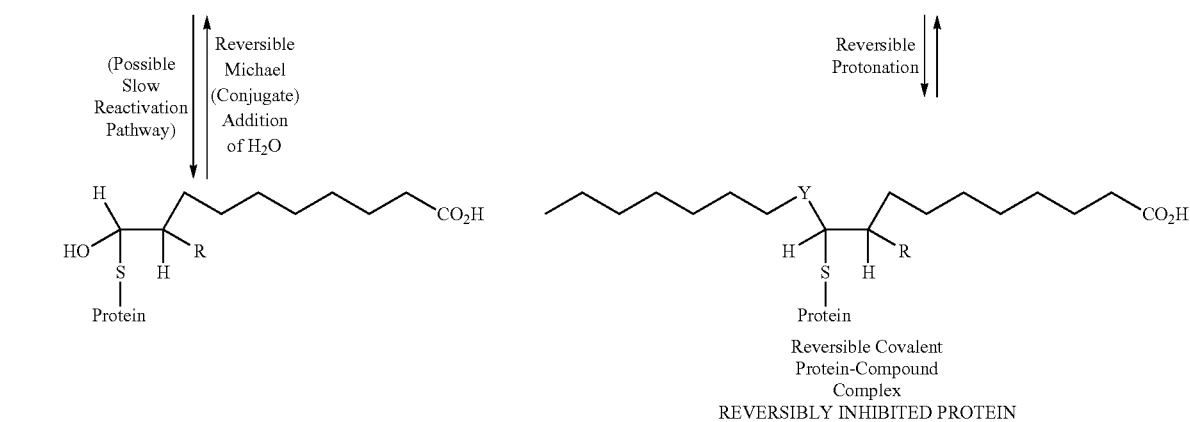

(Possible Slow Reactivation Pathway) | Reversible Michael (Conjugate) Addition of $H_2O$ Reversible Protonation Reversible Covalent Protein-Compound Complex
REVERSIBLY INHIBITED PROTEIN

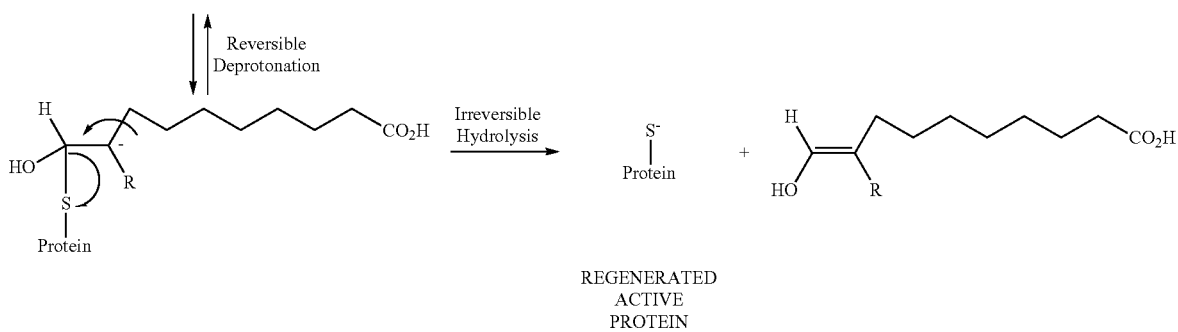

Reversible Deprotonation

Irreversible Hydrolysis

REGENERATED ACTIVE PROTEIN

Reversible Protonation

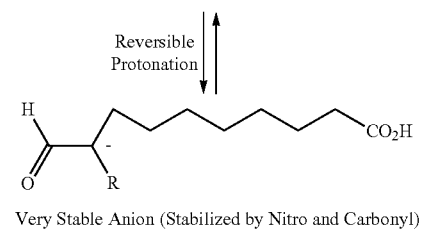

Very Stable Anion (Stabilized by Nitro and Carbonyl)

As shown in Mechanism II upon binding, a Michael reaction may occur between the thiol containing amino acid of the protein active site and the carbon-carbon double bond of the functionally-enhanced fatty acid inhibitor. In some embodiments, the resulting intermediate may undergo a reversible protonation creating a reversible covalent bond. This reversible covalent bond may allow the fatty acid inhibitor to form a more permanent bond with the protein which may reduce the activity of the binding protein by limiting the availability of the active site for other substrates, or the reversible covalent bond may allow for more long term or improved activation of the binding protein. In other embodiments, the double bond may reform after the Michael reaction dissociating the leaving group and any portion of the fatty acid associated with the leaving from the functionally-enhanced fatty acid inhibitor and fixing the covalent bond. Because the leaving group and any portion of the fatty acid associated with the leaving group may no longer bound by the protein after fixation of the covalent bond between the thiol and the remainder of the fatty acid inhibitor, it may dissociate from the complex as illustrated in Mechanism II. This may result in permanent irreversibly inhibition of the protein as the portion of the functionally-enhanced fatty acid inhibitor remaining covalently bound to the protein will occupy the active site. However, the covalent bond may be reversed in the presence of water, which may allow for deprotonation of the complex and eventually hydrolysis of the covalent bond. After hydrolysis the fatty acid inhibitor may dissociate from the active site of the protein essentially reactivating the protein, or the covalent bond may reform prolonging inhibition. Thus, Group II fatty acid inhibitors binding may result in either short or long term inhibition of the binding protein.

Group III

Still other embodiments are directed to functionally-enhanced fatty acid inhibitors that may include a leaving group in the main chain of the fatty acid where the leaving group replaces a carbon flanking the carbon of the carbon-carbon associated with the electron withdrawing group and one carbon removed from the carbon-carbon double bond. For example in some embodiments, the Group II functionally-enhanced fatty acid inhibitors may be of Formulae VII, VIIa, VIII, or VIIIa:

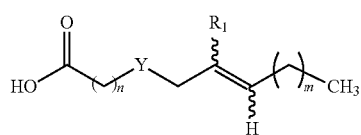
VII

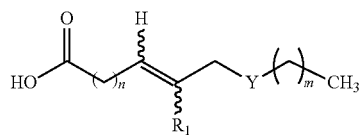
VIIa

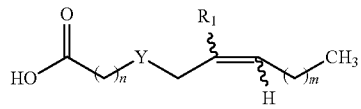
VIII

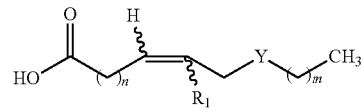
VIIIa where $R_1$ is an electron withdrawing group, and Y is a leaving group within the main chain such as, for example, —O—, —NR″—, —S—, —SO—, —SO$^2$—, —POR″—, and the like, and m and n can each individually be 1-20. In other embodiments, such compounds may include one or more double bonds flanking the electron withdrawing group containing carbon-carbon double bond. Some embodiments include compounds of general Formulae IX and IXa:

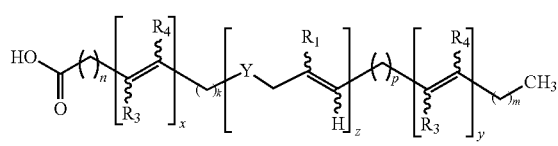
IX

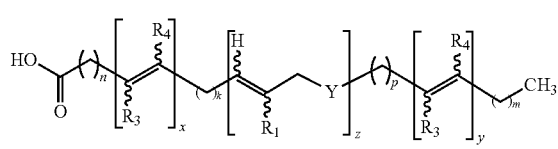
IXa where $R_1$ is an electron withdrawing group, and Y is a leaving group within the main chain, each $R_3$ and $R_4$ can, independently, be —H, an electron withdrawing group or a second functional group, m, n, k, and p can, independently, be 1-20, and each x, y, and z can independently be 0-5. In additional embodiments, functionally-enhanced fatty acid inhibitors such as those illustrated in Formulae VI and VIa may have additional heteroatoms located anywhere along the aliphatic chain, and in some embodiments, these heteroatoms may be associated with a carbon-carbon double bonds including an electron withdrawing group as illustrated in Formulae VII, VIIa, VIII, and VIIIa. In other embodiments, two or more Group III type moieties having electron withdrawing vinyl groups associated with a heteroatom at the gamma position on the aliphatic chain may be interspersed among additional carbon-carbon double bonds which may or may not have associated functional groups or additional functional groups. In certain exemplary embodiments, $R_1$ may be a nitro and Y may be sulfur.

Without wishing to be bound by theory, Group III functionally-enhanced fatty acid inhibitors may form a slowly reversible covalent bond with thiol containing amino acids in the active site of a binding protein. Formation of this slowly reversible covalent bond may provide permanent or long term inhibition of action of the protein or permanent or long term activation of the protein similar to that described under Groups I and II. The proposed mechanism of action is illustrated in Mechanism III:

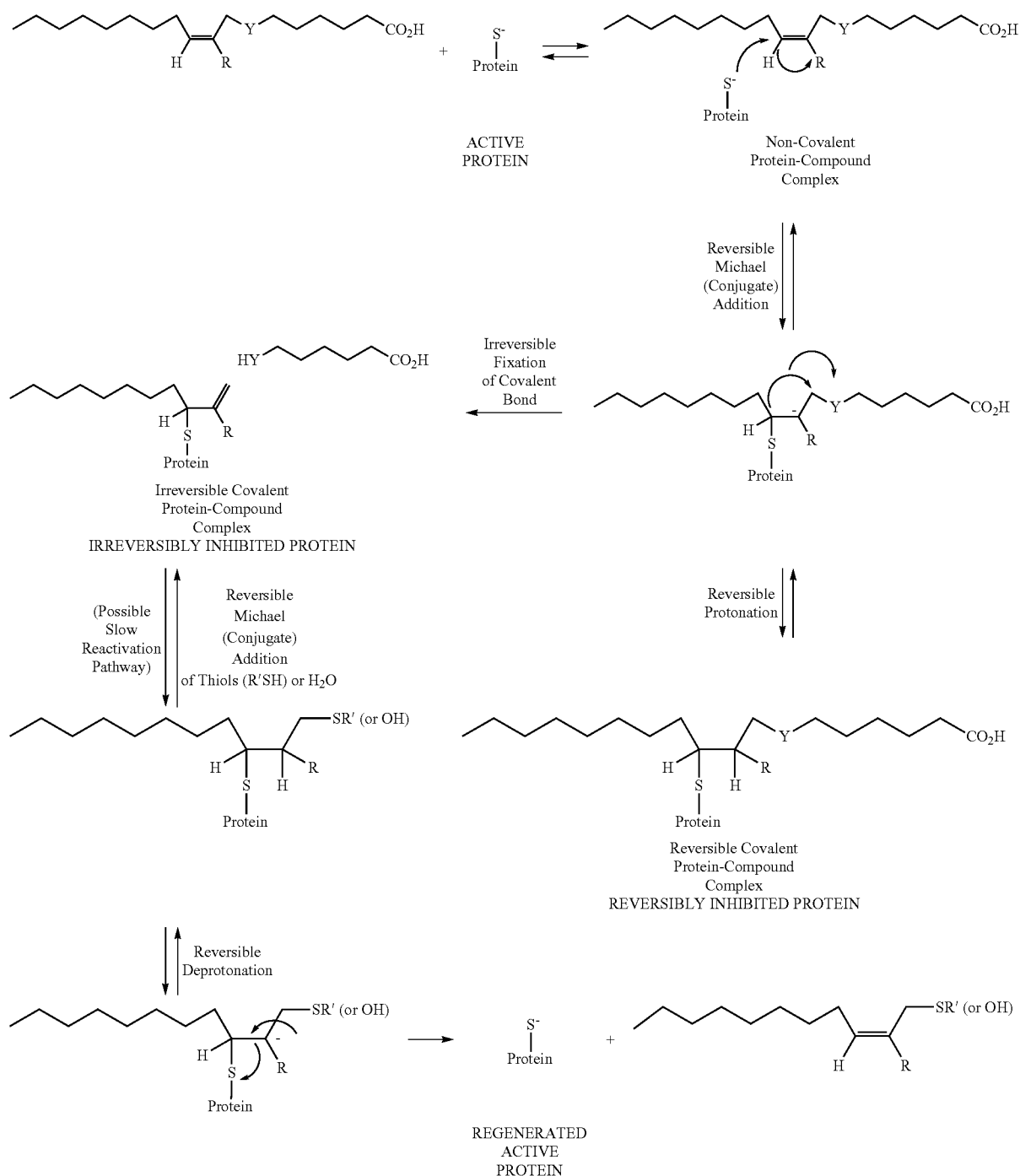

As illustrated in Mechanism III, a Michael addition with a thiol of a thiol containing amino acid in the active site of the binding protein may occur following binding of the functionally-enhanced fatty acid inhibitor to the protein. The intermediate created by this reaction may then undergo reversible protonation that may stabilize the covalent bond reversible inhibiting the protein by delaying dissociation of the fatty acid inhibitor until the protonation is reversed and the covalent bond is resolved. In other embodiments, the covalent bond may become fixed which may cause a double bond to form between the electron withdrawing group containing carbon and the intervening carbon between the electron withdrawing group and the leaving group. As a result of the carbon-carbon double bond formation, the bond between the leaving group and the intervening carbon may be broken and the portion of the functionally-enhanced fatty acid inhibitor may become dissociated from the active site of the protein. The remaining portion of the functionally-enhanced fatty acid inhibitor may remain covalently bound within the active site of the protein indefinitely. However, if the active site of the protein is accessible to water or another thiol containing fatty acid is available in the active site of the protein, a reversible deprotonation may occur that allows the newly formed double bond to be resolved and a subsequent hydrolysis may allow the covalent bond between the protein and the portion of the functionally-enhanced fatty acid inhibitor remaining in the active site to be broken releasing the fatty acid inhibitor. Thus, Group III functionally-enhanced fatty acid inhibitors binding may result in either short or long term inhibition of the binding protein.

Group IV

Some embodiments are directed to functionally-enhanced fatty acid inhibitors in which the carbon-carbon double bond associated with an electron withdrawing group is replaced by a strained heterocyclic ring. For example, in some embodiments, Group IV functionally-enhanced fatty acid inhibitors may be of Formulae X, XI, XII, and XIIa:

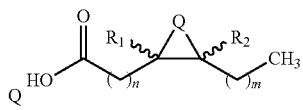

X

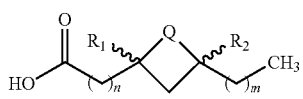

XI

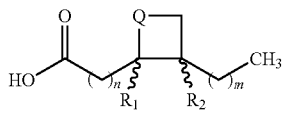

XII

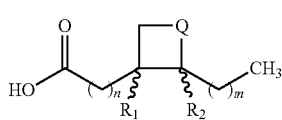

XIIa where one of $R_1$ or $R_2$ is an electron withdrawing group and the other is —H, Q can be any heteroatom, such as but not limited to —O—, —S—, —NR'''—, —CR'''$_2$—, and C=CR'''$_2$, where R''' can be —H, alkyl, alkeneyl, alkynyl, aryl, and the like, and m and n can, independently, be 1-20. Such embodiments therefore, include strained heterocycles including aziridines, episulfides, oxetanes, azetidines, and thiiranes. In other embodiments, the four carbon strained heterocycles may include two heteroatoms thereby encompassing dioxetanes and dithietanes, as well as, compounds that include a four carbon strained heterocycle with different heteroatoms. In other embodiments, such compounds may include one or more double bonds flanking the strained heterocyclic ring, and in still other embodiments, the compounds may include two or more strained heterocyclic rings.

In yet other embodiments, the strained heterocycle may be flanked by a carbonyl containing group such as, ketone, ester, amide, thioester, and the like. For example, in some embodiments, the Group IV compounds may be of Formulae XIII, XIV, XV, or XVa:

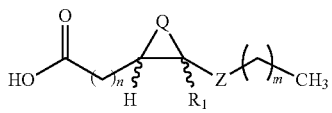

XIII

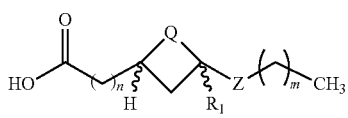

XIV

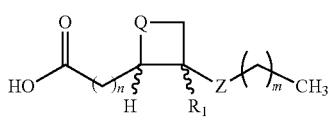

XV

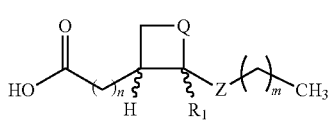

XVa or Formulae XVI, XVII, XVIII, or XVIIIa:

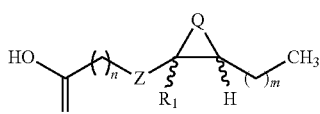

XVI

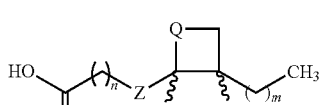

XVII

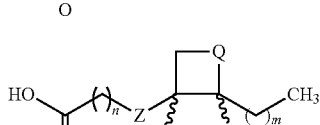

XVIII

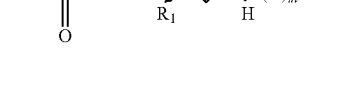

XVIIIa where $R_1$ is an electron withdrawing group, Q can be any heteroatom, such as, but not limited to, —O—, —S—, —NR'''—, —CR'''$_2$—, and C=CR'''$_2$, where R''' can be —H, alkyl, alkeneyl, alkynyl, aryl, and the like, Z can be a ketone, ester, amide, thioester, and the like, and each m and n can, independently, be 1-20. In particular exemplary embodiments, Group IV compounds may be:

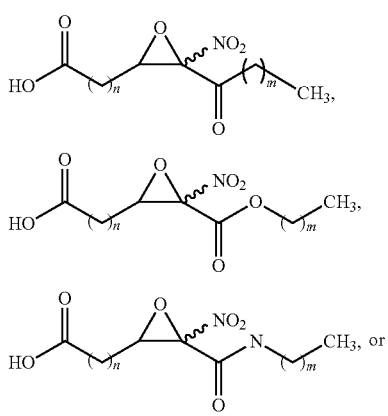

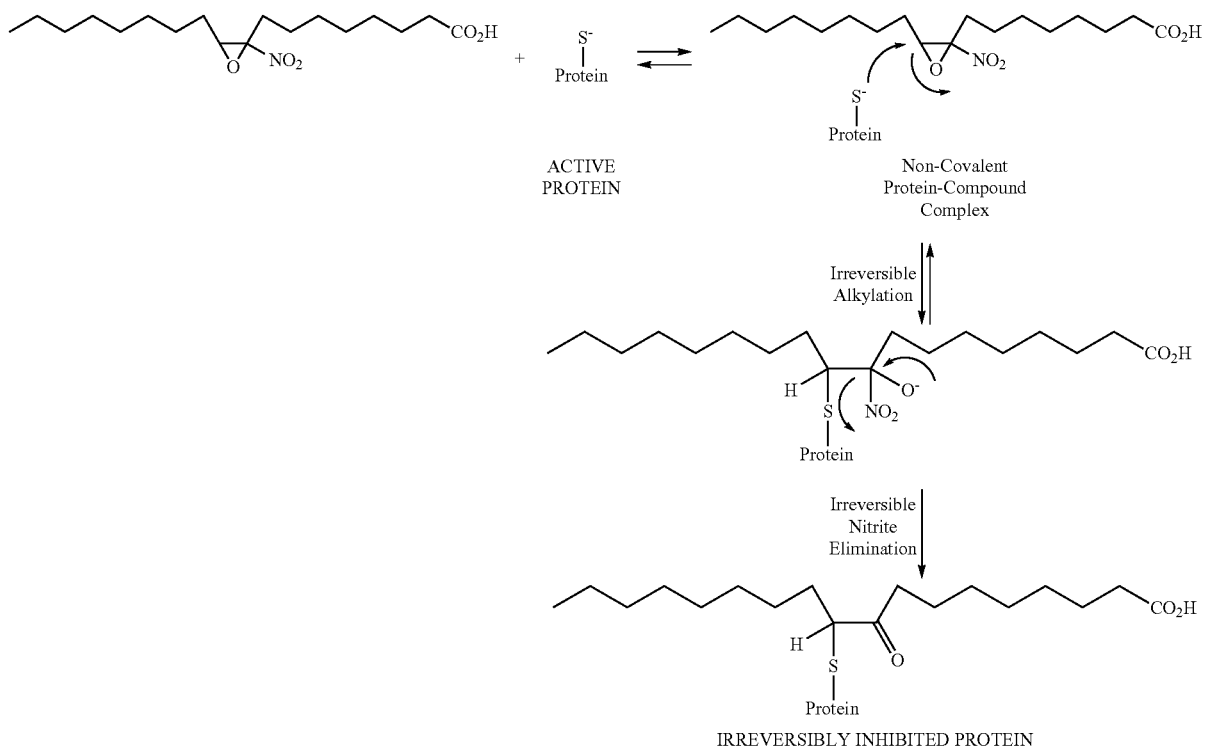

ACTIVE PROTEIN

Non-Covalent Protein-Compound Complex

Irreversible Alkylation

Irreversible Nitrite Elimination

IRREVERSIBLY INHIBITED PROTEIN

-continued

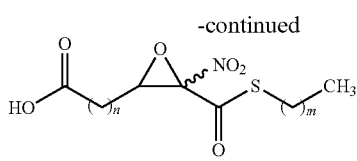

where each m and n can independently be 1-20. Such embodiments, include strained heterocycles including aziridines, episulfides, oxetanes, azetidines, and thiiranes. In other embodiments, the four carbon strained heterocycles may include two heteroatoms thereby encompassing dioxetanes and dithietanes, as well as, compounds that include a four carbon strained heterocycle with different heteroatoms. In other embodiments, such compounds may include two or more strained heterocyclic rings, and in still other embodiments, such compounds may include one or more double bonds flanking the strained heterocyclic ring. In further embodiments, two or more Group II type moieties having electron withdrawing vinyl groups associated with a heteroatom at the gamma position on the aliphatic chain may be interspersed among additional carbon-carbon double bonds which may or may not have associated functional groups or additional functional groups.

Without wishing to be bound by theory, Group IV functionally-enhanced fatty acid inhibitors may form an irreversible or slowly reversible covalent bond with thiol containing amino acids in the active site of a binding protein. Formation of this slowly reversible covalent bond may provide permanent or long term inhibition of action of the protein or permanent or long term activation of the protein similar to that described under Groups I, II, and III. Functionally-enhanced fatty acid inhibitors having a strained heterocycle may react with thiol containing amino acids to form a covalent bond in several ways. For example, one proposed mechanism of action is illustrated in Mechanism IV:

As illustrated in Mechanism IV, the thiol group of an active site amino acid may interact with the strained heterocycle and undergo an irreversible alkylation, which may result in a covalent bond between the thiol and the carbon adjacent to the carbon associated with the electron withdrawing group. The electron withdrawing group may then be eliminated by, for example the nitrite elimination illustrated above leaving, for example, a carbonyl. The covalent bond created between the thiol and the functionally-enhanced fatty acid inhibitor resulting from this mechanism is irreversible. Therefore, the use of Group IV fatty acid inhibitors may result in permanent inhibition of the binding protein.

Another proposed mechanism for action of functionally-enhanced fatty acid inhibitors including strained heterocycle is provided in Mechanism V:

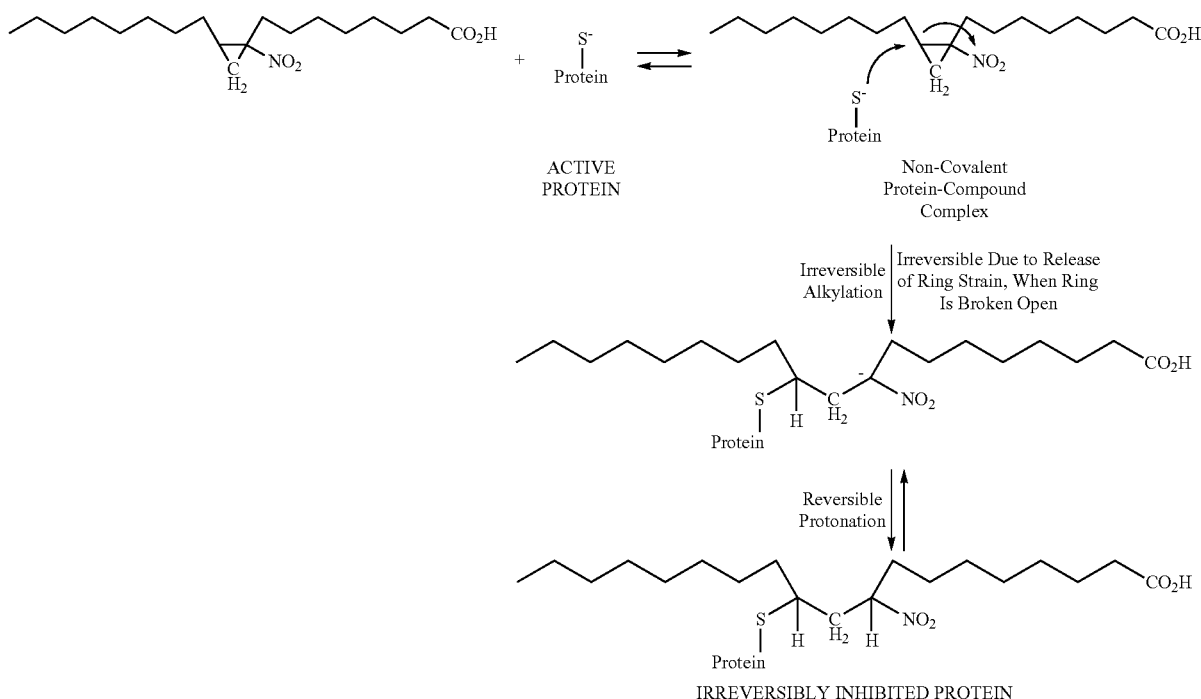

In Mechanism V, the thiol of the active site amino acid may associate with the carbon adjacent to the electron withdrawing group, $NO_2$, in this exemplary embodiment, and following alkylation, the ring may open forming, for example, a continuous alkyl chain as illustrated in Mechanism V, or providing a heteroatom on the alkyl chain where Q is a heteroatom. While reversible protonation may occur, the mechanism by which the covalent bond formed between the thiol of the active site amino acid and the functionally-enhanced fatty acid inhibitor is formed is irreversible and may result in permanent inhibition of the binding protein. Therefore, the use of Group IV functionally-enhanced fatty acid inhibitors may result in permanent inhibition of the binding protein.

For ease of understanding, the functionally-enhanced fatty acid inhibitors of various embodiments have been described separately; however, in some embodiments, fatty acid inhibitors may include more than one class of inhibitor moieties. For example, embodiments include functionally-enhanced fatty acid inhibitors that incorporate any combination of Group I type inhibitor moieties, a Group II type inhibitor moieties, a Group III type inhibitor moieties, and Group IV type inhibitor moieties. In other embodiments, functionally-enhanced fatty acid inhibitors may further include electron withdrawing vinyl or electron withdrawing allylic groups such as those described in U.S. application Ser. Nos. 11/568, 377 and 12/433,130, which are hereby incorporated by reference in its entirety, or any other functional groups or heteroatoms known in the art. Without wishing to be bound by theory, functionally-enhanced fatty acid inhibitors having additional functional groups outside the Group I-IV type moieties described above may modify the activity of the functionally-enhanced fatty acid inhibitors by, for example, increasing availability of the compound to target tissues and cells.

In still other embodiments, the carboxy-terminal end of the functionally-enhanced fatty acid inhibitors may be modified. For example, in some embodiments, the fatty acid may include a glycerol associated with the carboxy-terminal end of the fatty acid to create a glycerolipid, and such glycerolipids may be mono-, di-, or tri-glycerides wherein at least one of the fatty acids of a di- or tri-glyceride may be a functionally-enhanced fatty acid inhibitor and any remaining fatty acids may be a saturated or unsaturated fatty acid. Similarly, in other embodiments, a carbohydrate may be associated with the carboxy-terminal end of a fatty acid inhibitor to form a glycolipid. In such embodiments, any carbohydrate known in the art may be a carbohydrate moiety of a glycolipid including, but not limited to, galactose and glucose. In yet other embodiments, a carbohydrate may be associated with a glyceride which is associated with the carboxy-terminal end of a fatty acid inhibitor to form a glycero-glycolipid, which may have one or two fatty acid inhibitors associated with the glycero-portion of the glycero-glycolipid and, in embodiments in which only one fatty acid inhibitor is associated with the glycero-glycolipid, the remaining position on the glycerol may include a saturated or unsaturated fatty acid or hydrogen, alkyl, or a functional group such as, for example, alcohol, amine, phosphate, phosphonic acid, thiol, sulfonic acid and the like. In certain embodiments, the carboxy-terminal end of the fatty acid inhibitors of the invention may be associated with a phosphate to from a phospholipid. In such embodiments, the phosphate may be directly associated with the fatty acid through the carboxy-terminus, or the phosphate may be associated with a di-glyceride wherein one or two fatty acid inhibitors are attached glycerol moiety and, in embodiments where only one activated the fatty acid is attached to the glycerol, remaining position on the glycerol may include a saturated or unsaturated fatty acid or hydrogen, alkyl, or a functional group such as, for example, alcohol, amine, phosphate, phosphonic acid, thiol, sulfonic acid and the like. In further embodiments, the carboxy-terminus of the fatty acid inhibitor may be associated with a cholesterol or other sterol moiety. In yet other embodiments, the carboxy-terminal end may be modified by the covalent attachment of a secondary active agent. In the particular embodiments, carboxy-terminal modifications including a glycerol may not include a nitro group. Without wishing to be bound by theory, modification of the carboxy-terminal end of fatty acid inhibitors may enhance partitioning of the fatty acid inhibitor after administration and may also improve resilience of the fatty acid inhibitor by inhibiting beta-oxidation in mitochondria following administration.

The functionally-enhanced fatty acid inhibitors described above may be prepared as a pharmaceutically acceptable formulation. The term "pharmaceutically acceptable" is used herein to mean that the compound is appropriate for use in a pharmaceutical product. For example, pharmaceutically acceptable cations include metallic ions and organic ions. More preferred metallic ions include, but are not limited to, appropriate alkali metal salts, alkaline earth metal salts and other physiological acceptable metal ions. Exemplary ions include aluminum, calcium, lithium, magnesium, potassium, sodium and zinc in their usual valences. Preferred organic ions include protonated tertiary amines and quaternary ammonium cations, including in part, trimethylamine, diethylamine, N,N'-dibenzylethylenediamine, chloroprocaine, choline, diethanolamine, ethylenediamine, meglumine(N-methylglucamine) and procaine. Exemplary pharmaceutically acceptable acids include, without limitation, hydrochloric acid, hydroiodic acid, hydrobromic acid, phosphoric acid, sulfuric acid, methanesulfonic acid, acetic acid, formic acid, tartaric acid, maleic acid, malic acid, citric acid, isocitric acid, succinic acid, lactic acid, gluconic acid, glucuronic acid, pyruvic acid, oxalacetic acid, fumaric acid, propionic acid, aspartic acid, glutamic acid, benzoic acid, and the like.

Isomeric and tautomeric forms of functionally-enhanced fatty acid inhibitors described herein and regioisomers as well as pharmaceutically acceptable salts of these compounds are also encompassed by the invention. Exemplary pharmaceutically acceptable salts are prepared from formic, acetic, propionic, succinic, glycolic, gluconic, lactic, malic, tartaric, citric, ascorbic, glucuronic, maleic, fumaric, pyruvic, aspartic, glutamic, benzoic, anthranilic, mesylic, stearic, salicylic, p-hydroxybenzoic, phenylacetic, mandelic, embonic (pamoic), methanesulfonic, ethanesulfonic, benzenesulfonic, pantothenic, toluenesulfonic, 2-hydroxyethanesulfonic, sulfanilic, cyclohexylaminosulfonic, algenic, .beta.-hydroxybutyric, galactaric and galacturonic acids.

Suitable pharmaceutically acceptable base addition salts used in connection with the functionally-enhanced fatty acid inhibitors include metallic ion salts and organic ion salts. Exemplary metallic ion salts include, but are not limited to, appropriate alkali metal (group Ia) salts, alkaline earth metal (group IIa) salts and other physiological acceptable metal ions. Such salts can be made from the ions of aluminum, calcium, lithium, magnesium, potassium, sodium and zinc. Preferred organic salts can be made from tertiary amines and quaternary ammonium salts, including in part, trimethylamine, diethylamine, N,N'-dibenzylethylenediamine, chloroprocaine, choline, diethanolamine, ethylenediamine, meglumine (N-methylglucamine) and procaine. All of the above salts can be prepared by those skilled in the art by conventional means from the corresponding compound of the present invention.

Functionally-enhanced fatty acid inhibitors as described in various embodiments above, may be administered to individuals to treat, ameliorate and/or prevent a number both acute and chronic inflammatory and metabolic conditions. In particular embodiments, functionally-enhanced fatty acid inhibitors may be used to treat acute conditions including general inflammation, autoimmune disease, autoinflammatory disease, arterial stenosis, organ transplant rejection and burns, and chronic conditions such as, chronic lung injury and respiratory distress, diabetes, hypertension, obesity, arthritis, neurodegenerative disorders and various skin disorders. However, in other embodiments, functionally-enhanced fatty acid inhibitors may be used to treat any condition having symptoms including chronic or acute inflammation, such as, for example, arthritis, lupus, Lyme's disease, gout, sepsis, hyperthermia, ulcers, enterocolitis, osteoporosis, viral or bacterial infections, cytomegalovirus, periodontal disease, glomerulonephritis, sarcoidosis, lung disease, lung inflammation, fibrosis of the lung, asthma, acquired respiratory distress syndrome, tobacco induced lung disease, granuloma formation, fibrosis of the liver, graft vs. host disease, postsurgical inflammation, coronary and peripheral vessel restenosis following angioplasty, stent placement or bypass graft, coronary artery bypass graft (CABG), acute and chronic leukemia, B lymphocyte leukemia, neoplastic diseases, arteriosclerosis, atherosclerosis, myocardial inflammation, psoriasis, immunodeficiency, disseminated intravascular coagulation, systemic sclerosis, amyotrophic lateral sclerosis, multiple sclerosis, Parkinson's disease, Alzheimer's disease, encephalomyelitis, edema, inflammatory bowel disease, hyper IgE syndrome, cancer metastasis or growth, adoptive immune therapy, reperfusion syndrome, radiation burns, alopecia and the like.

When administered, functionally-enhanced fatty acid inhibitors may interact with a number of cellular receptors and/or proteins that mediate inflammation, either by inhibiting or stimulating their activity thereby inhibiting or reducing inflammation. Without wishing to be bound by theory, functionally-enhanced fatty acid inhibitors may modulate important signaling activities including, for example, neurotransmission, gene expression, vascular function and inflammatory responses, and chemical properties of functionally-enhanced fatty acid inhibitors that may facilitate these activities include, but are not limited to, the strong, reversible electrophilic nature of the β carbon adjacent to the electron withdrawing vinyl group, an ability to undergo Nef-like acid base reactions to release NO, an ability to partition into both hydrophobic and hydrophilic compartments, and a strong affinity for G-protein coupled receptors and nuclear receptors.

For example, in one embodiment, functionally-enhanced fatty acid inhibitors may be administered to mediate cell signaling via multiple G-protein coupled receptors and nuclear receptors such as, but not limited to, peroxisome proliferator-activated receptors (PPAR) including PPARα, PPARγ, and PPARδ. PPAR is a nuclear receptor that is expressed throughout an organism, including in monocytes/macrophages, neutrophils, endothelial cells, adipocytes, epithelial cells, hepatocytes, mesangial cells, vascular smooth muscle cells, neuronal cells and when "activated" induces transcription of a number of target genes. Activation of PPAR has been shown to play various roles in regulating tissue homeostasis including, for example, increasing insulin sensitivity, suppress chronic inflammatory processes, reduce circulating free fatty acid levels, correct endothelial dysfunction, reduce fatty streak formation, delay plaque formation, limit blood vessel wall thickening and enhance plaque stabilization and regression. The fatty acid inhibitors embodied herein may perform each of these functions associated with PPAR activation.

Moreover, functionally-enhanced fatty acid inhibitors may perform these functions without significantly altering normal cellular process. For example, in one embodiment, a fatty acid inhibitor may be administered to treat hypertension by lowering blood pressure to normal levels without reducing the blood pressure of the individual below normal levels even if the fatty acid inhibitor is over-administered. Thus, without wishing to be bound by theory, the fatty acid inhibitors may provide treatment of an individual without the negative affects associated with over-administration or over-treatment using traditional medications.

Activation of PPAR has been shown to be induced either directly or in part by a locking reaction in which a critical thiol in a highly conserved cysteine (Cys 285 of human PPARγ) which is located in a ligand binding domain of PPAR. Partial activation of PPAR has been shown to occur when relatively high concentrations of known thiol reactive compounds, such as 15-deoxy-$\Delta^{12,14}$-prostaglandin $J_2$ (15-d $PGJ_2$), are administered. Without wishing to be bound by theory, fatty acid inhibitors may bind to PPAR covalently at the reactive thiol in the ligand binding domain of PPAR. Moreover, fatty acid inhibitors may induce a conformational change in PPAR. More specifically, fatty acid inhibitor binding may result in the C-terminus of the ligand binding domain (α-helix 12) to adopt an active conformation that may promote a beneficial pattern of co-repressor release and co-activator recruitment. Thus, fatty acid inhibitors may enhance PPAR activation and transcription of PPAR regulated genes beyond that of known PPAR activating compounds.

In addition to activation of PPAR, fatty acid inhibitor administration may be useful for activating a number of other factors important for cell signaling. For example, in one embodiment, fatty acid inhibitors may be administered to induce gene expression and tissue activity of heme oxygenase-1 (HO-1) which has been shown to mediate adaptive and protective responses during inflammation, and activation of an adaptive or protective inflammatory response mediated by HO may be useful in treating inflammatory diseases such as, but not limited to, atherosclerosis, acute renal failure, vascular restinosis, transplant rejection, and sepsis. In another embodiment, fatty acid inhibitors may induce a reversible post-translational modification of proteins, such as, for example, glutathione (GSH) and glyceraldehyde-3-phosphate dehydrogenase (GAPDH) by covalently binding to catalytic cysteines on such proteins. Without wishing to be bound by theory, the covelent modification of these proteins by fatty acid inhibitors may increase the hydrophobicity of these proteins inducing translocation of to membranes and suggests a role for redox regulation of enzyme function, cell signaling and protein trafficking. In yet another embodiment, fatty acid inhibitors may be administered to repress NF-κB dependent gene expression and endothelial tumor necrosis factor-α induced expression of vascular cell adhesion molecules in monocytes and macrophages which results in inhibition of rolling and adhesion during inflammation. Thus, fatty acid inhibitors may be useful for treating general inflammation resulting from surgery, injury or infection. In a further embodiment, fatty acid inhibitors may be administered to limit tissue inflammatory injury and inhibit the proliferation of vascular smooth muscle cells by increasing cellular levels of nuclear factor erythroid 2-related factor-2 (Nrf-2) which may be useful in the treatment of a number of vascular diseases. In some embodiments, fatty acid inhibitors may be administered to modify the activity of transient receptor potential (TRP) channels such as TRPA1 and TRPV1 and may be capable of modifying pain and inflammatory signaling. In other embodiments, fatty acid inhibitors may be used to induce heat shock factor (HSF) proteins and inhibit protein tyrosine phosphatases (PTPs), and in still other embodiments, fatty acid inhibitors may be administered to activate mitogen-activated protein kinases (MAP kinases).

In a still further embodiment, functionally-enhanced fatty acid inhibitors may be useful for ischemic preconditioning. For example, nitrated fatty acids produced by mitochondria in cells under ischemic conditions cause a number of physiological changes within the cell that increases cell survival under ischemic conditions. By providing fatty acid inhibitors to an individual, similar ischemic preconditioning may be achieved allowing for improved survival of, for example, cardiac tissue under ischemic conditions or organs being preserved for optimizing viability and function upon transplantation.

Because functionally-enhanced fatty acid inhibitors form a more stable interaction within the active site of the target protein than the native substrate, the beneficial effects of functionally-enhanced fatty acid inhibitors described above may be observed following a single administration of the functionally-enhanced fatty acid inhibitor and may continue to be observed for a period of from several days to weeks or months. Additionally, the stability of the covalent bond formed with the active site thiol containing amino acid may affect the amount of fatty acid inhibitor necessary to elicit a response. For example, Group IV functionally-enhanced fatty acid inhibitors, which form a permanent covalent bond with an active site thiol containing amino acid may be permanently activate or inhibit the target protein, and the effect of administration such a fatty acid inhibitor may be reduced only based on turnover of the target protein. Thus, less frequent and lower doses of the functionally-enhanced fatty acid inhibitors of embodiments may be necessary to produce the desired effect than other forms of treatment.

The functionally-enhanced fatty acid inhibitors of embodiments can be administered in any conventional manner by any route where they are active. Administration can be systemic or local. For example, administration can be, but is not limited to, parenteral, subcutaneous, intravenous, intramuscular, intraperitoneal, transdermal, oral, buccal, or ocular routes, or intravaginally, by inhalation, by depot injections, or by implants. In certain embodiments, the administration may be parenteral or intravenous, all in the presence or absence of stabilizing additives that favor extended systemic uptake, tissue half-life and intracellular delivery. Thus, modes of administration for the compounds of the present invention (either alone or in combination with other pharmaceuticals) can be injectable (including short-acting, depot, implant and pellet forms injected subcutaneously or intramuscularly). In some embodiments, an injectable formulation including a fatty acid inhibitor may be deposited to a site of injury or inflammation, such as, for example, the site of a surgical incision or a site of inflammation due to arthroscopy, angioplasty, stent placement, by-pass surgery and so on.

In certain other embodiments, functionally-enhanced fatty acid inhibitors may be applied locally as a salve or lotion applied directly to an area of inflammation. For example, in some embodiments, a lotion or salve including fatty acid inhibitors of the invention may be prepared and applied to a burn, radiation burn, site of dermal disorder, edema, arthritic joint or the like.

Various embodiments are also directed to method for administering functionally-enhanced fatty acid inhibitors. Specific modes of administration may vary and may depend on the indication. The selection of the specific route of administration and the dose regimen may be adjusted or titrated by the clinician according to methods known to the clinician in order to obtain the optimal clinical response. The amount of compound to be administered is that amount which is therapeutically effective. The dosage to be administered will depend on the characteristics of the subject being treated, e.g., the particular animal treated, age, weight, health, types of concurrent treatment, if any, and frequency of treatments, and can be easily determined by one of skill in the art (e.g., by the clinician). Those skilled in the art will appreciate that dosages may be determined with guidance, for example, from Goodman & Goldman's The Pharmacological Basis of Therapeutics, Ninth Edition (1996), Appendix II, pp. 1707-1711 or from Goodman & Goldman's The Pharmacological Basis of Therapeutics, Tenth Edition (2001), Appendix II, pp. 475-493 both of which are hereby incorporated by reference in their entireties. With respect to conventional prenylation enzyme inhibitors, guidance may be obtained from art-recognized dosage amounts as described, for example, by J. E. Karp, et al., Blood, 97(11):3361-3369 (2001) and A. A. Adjei, et al., Cancer Research, 60:1871-1877 (2000) hereby incorporated by reference in its entirety.

In various embodiments, an effective amount of a functionally-enhanced fatty acid inhibitor delivered during each administration cycle may range from about 10 mg/m$^2$/day to about 1000 mg/m$^2$/day. In some embodiments, an effective amount may be about 20 mg/m$^2$/day to about 700 mg/m$^2$/day, and in others, an effective amount may be about 30 mg/m$^2$/day to about 600 mg/m$^2$/day. In particular embodiments, an effective amount may be about 50 mg/m$^2$/day, about 400 mg/m$^2$/day, about 500 mg/m$^2$/day, or about 600 mg/m$^2$/day. In yet other embodiments, an effective amount of a fatty acid inhibitor may vary as treatment progresses. For example, a dosage regimen may be increased or decreased as treatment proceeds through administration cycles, or the daily dosage may increase or decrease throughout administration. In additional embodiments, greater than 1000 mg/m$^2$/day may be administered because even high doses of fatty acid inhibitor are generally tolerable to the patient and may not produce undesired physiological effects.

In some embodiments, the dosage regimen as described above may be combined with a secondary form of treatment or a secondary agent The fatty acid inhibitors of various embodiments may be prepared by any method known in the art. For example, in one embodiment, a fatty acid inhibitor may be prepared by:

i) contacting an unsaturated fatty acid with a mercuric salt and a selenium compound;

ii) contacting the intermediate resulting from step a) with a reagent or reactant that can introduce an electron withdrawing group; and iii) reacting the intermediate resulting from step b) with an oxidizing agent.

Without wishing to be bound by theory, a selenium compound, such as, for example, PhSeBr, PhSeCl, PhSeO$_2$CCF$_3$, PhSeO$_2$H, PhSeCN and the like, may react with one or more carbon-carbon double bond of the unsaturated fatty acid to form a three-membered ring intermediate on the fatty acid in a reaction that may be facilitated by the mercuric salt such as, for example, HgCl$_2$, Hg(NO$_3$)$_2$, Hg(OAc)$_2$ and the like as depicted in step I of the reaction below:

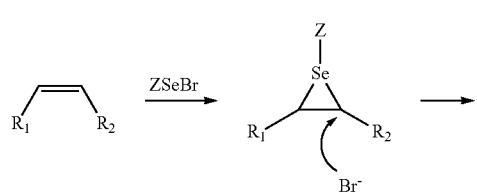

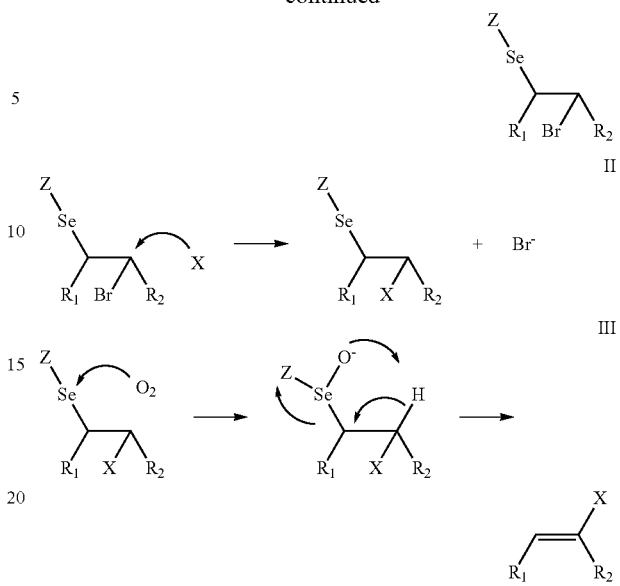

The source of the electron withdrawing group may be any compound known in the art that is capable of generating an electron withdrawing group that can be incorporated into the fatty acid inhibitor, such as, for example, NaNO$_2$, AgNO$_2$, HSO$_2$OH, and the like. Without wishing to be bound by theory, the electron withdrawing group (X in the reaction scheme above) may become joined to the hydrocarbon chain by displacing, for example, the bromine that was associated with the selenium compound as depicted in step II of the reaction scheme provided above. It is noted that the electron withdrawing groups may also react directly with the three-membered ring episelenonium ion shown in step I at the position where the bromine is shown as attacking. Finally, as depicted in step III of the reaction scheme provided above, the oxidizing agent forms a reactive selenium-oxo functional group, which undergo molecular rearrangement and elimination of ZSeOH leading to formation of the electron withdrawing vinyl (depicted as a nitro vinyl) on the hydrocarbon chain. Z in the reaction scheme above may be any number of groups. For example, in certain embodiments, Z may be a phenyl group.

In other embodiments, a fatty acid inhibitor may be prepared using a modified aldol condensation such as the Henry reaction. A review of the Henry reaction and methods related to the Henry method can be found, for example, in Frederick A. Luzzio, F. A. "The Henry reaction: recent examples" Tetrahedron 2001, 57, 915-945 which is hereby incorporated by reference in its entirety. Known variations of the Henry reaction may also be useful in preparing fatty acid inhibitors and all such methods are embodied herein. For example, in some embodiments, variations of the Henry reaction including, but not limited to, the Wittig-like variation of the Henry reaction, the Horner-Wadsworth-Emmons variation of the Henry reaction, and the Peterson-olefination variation of the Henry reaction. In such methods, double bonds are formed using the assistance of groups temporarily included in the reactants but that do are not included in the product. For example, the Wittig reaction uses phosphorus ylides to aid in the condensation reactions with carbonyls and in the dehydration reaction to form alkenes. The Horner-Wadsworth-Emmons reaction uses phosphonate esters, and the Peterson olefination uses silicon reagents for the condensation and dehydration steps. A review of major alkene-forming name reactions by reaction of a functionalized reagent with a carbonyl compound including the Wittig reaction, Horner-Wittig, Horner-Wadsworth-Emmons can be found, for example, in Peterson, Johnson, and Julia reactions. Blakemore, P. R. "The modified Julia olefination: alkene synthesis via the condensation of metallated heteroarylalkylsulfones with carbonyl compounds *J. Chem. Soc., Perkin Trans.* 1, 2002, 2563-2585 which is hereby incorporated by reference in its entirety.

The Henry "nitro-aldol" reaction is the condensation of a nitroalkane with either an aldehyde or a ketone carbonyl containing compound to form a nitro-aldo product with the newly-formed beta-hydroxynitroalkyl group. Dehydration (loss of water) from nitro-aldol products leads to the formation of nitroalkenes. There are many methods to perform the nitroalkane-carbonyl condensation reaction to make nitro-aldols and there are many methods for the dehydration reaction to form nitroalkenes. Examples of such methods can be found in, for example, Woodcock, S. R.; Marwitz, A. J. V. Bruno, P.; Branchaud, B. P. "Synthesis of Nitrolipids. All Four Possible Diastereomers of Nitrooleic Acids: (E)- and (Z)-, 9- and 10-Nitro-octadec-9-enoic Acids" *Organic Letters*, 2006, 8, 3931-3934 which provides one regioisomer and usually one of two possible alkene cis/trans or Z/E diastereomers, in high purity and usually in high chemical yield, which is hereby incorporated by reference in its entireties.

Enantioselective Henry reactions are also possible and may require the use of one or more catalysts for the reaction, and embodiments of the invention, include the use of such methods to prepare stereospecific isomers of nitroalkenes. For example, Boruwa, J.; Gogoi, N.; Saikia, P. P.; and Barua, N. C. "Catalytic Asymmetric Henry Reaction" *Tetrahedron: Asymmetry* 2006, 17, 3315-3326 which is hereby incorporated by reference in its entirety, describes methods for preparing stereospecific isomers of nitoralkenes.

In still other embodiments, alkenes (olefins) may be prepared by metal-mediated cross coupling reactions (joining together of two molecules to make one new molecule) by condensation onto a carbonyl compound. Such methods have not been applied to the formation of nitroalkenes or to the formation of other alkenes with electron-withdrawing substituents, but such methods could be adapted to the synthesis of alkenes with electron-withdrawing substituents. For example, named cross coupling reactions such as the Heck, Suzuki and Stille coupling, along with others may be used to prepare fatty acid inhibitors. Such methods are well known in the art. A review of such reactions of can be found in, for example, Metal-Catalyzed Cross-Coupling Reactions de Meijere, Armin/Diederich, Francois (eds.) Wiley-VCH, Weinheim 2004. XXII, ISBN-10: 3-527-30518-1 and ISBN-13: 978-3-527-30518-6 which are hereby incorporated by reference in their entireties.

Examples of various embodiments of methods for preparing fatty acid inhibitors may at least include the following steps:

i) combining a first component at least including an aliphatic hydrocarbon having an electron withdrawing group at one end with an second component including aliphatic hydrocarbon chain having an aldehyde at one end in the presence of a base to form a first intermediate; and ii) generating an alkene from the first intermediate.

Exemplary reactions are presented in schemes I and II below:

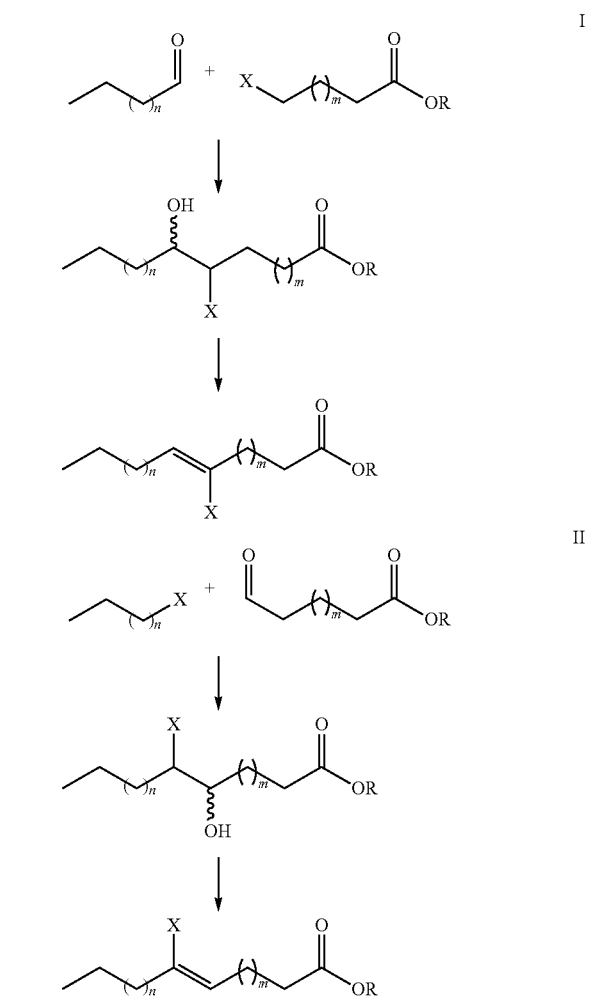

In reaction schemes I and II, the variable X represents an electron withdrawing group and can be any electron withdrawing group discussed herein above or known in the art. The variables n and m represent a number of carbon atoms in the aliphatic hydrocarbon chain, and n and m can be any number. For example, the aliphatic hydrocarbon chains of any of the starting compound may be from 2-20 carbons in length. Moreover, the position of the double bond and the arrangement of the electron withdrawing group in relation to the double bond may be determined specifically, and particular fatty acid inhibitors may be created in high yield. For example, an oleic acid may be produced by the reaction of scheme I by combining a first substrate where m is 10 and a second substrate where n is 2.

Any fatty acid inhibitor may be produced using the method presented above, and both naturally-occurring and non-naturally-occurring analogs may be synthesized. For example, synthesis of an exemplary nitrated fatty acids may be produced as illustrated in the general synthetic method is shown in scheme III, below.

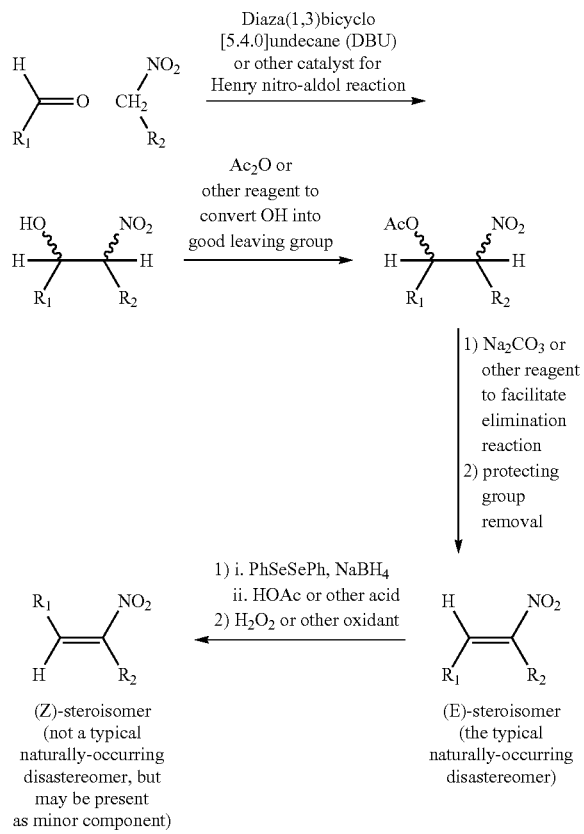

In such embodiments, $R_1$ and $R_2$ can include any number of carbons. For example in one embodiment, a naturally occurring fatty acid having an even number of carbons (20 carbons total, in this case) may be prepared from components where $R_2$ is $CH_2CH_3$ and $R_1$ is $(CH_2)_{15}CO_2R_3$, where $R_3$ is a protecting group for the carboxylic acid functional group found in fatty acids. Similarly, a non-naturally occurring fatty acid having an odd number of carbons (19 carbons total, in this case) may be prepared from components where $R_2$ is $CH_2CH_3$ and $R_1$ is $(CH_2)_{14}CO_2R_3$, where $R_3$ is a protecting group for the carboxylic acid functional group found in fatty acids. The method illustrated in scheme III can be applied to the synthesis of essentially any nitrated lipid having either an even or an odd number of carbons by incorporating different $R_1$ and $R_2$ groups. For example, each of $R_1$ and $R_2$ may be an aliphatic or substituted aliphatic carbon chain having from 1 to 20 carbons, although any greater number of carbons is also possible. Moreover, individual $R_1$ and/or $R_2$ groups may include any number of carbon-carbon double bonds, which may or may not include associated electron withdrawing groups attached to an alpha, beta, or gamma carbon of the carbon-carbon double bond. Similarly, individual $R_1$ and $R_2$ groups may include branched chains. In such embodiments, the additional carbon-carbon double bonds associated with $R_1$ and/or $R_2$ may be conjugated, unconjugated, or partially conjugated with one another or will become conjugated with a carbon-carbon double bond created as a result of the reaction. As indicated above, the reaction depicted in scheme III may be carried out sequentially to create a fatty acid inhibitor having more than one carbon-carbon double bond with associated electron withdrawing groups. In such embodiments, individual $R_1$ and $R_2$ groups for each reaction in a sequence may be from 1 to about 12 carbons, although any greater number of carbons is also possible.

Group I functionally-enhanced fatty acid inhibitors may be formed by any method known in the art. For example, in some embodiments, an activated fatty acid prepared as described above may be further modified as describe in scheme IV:

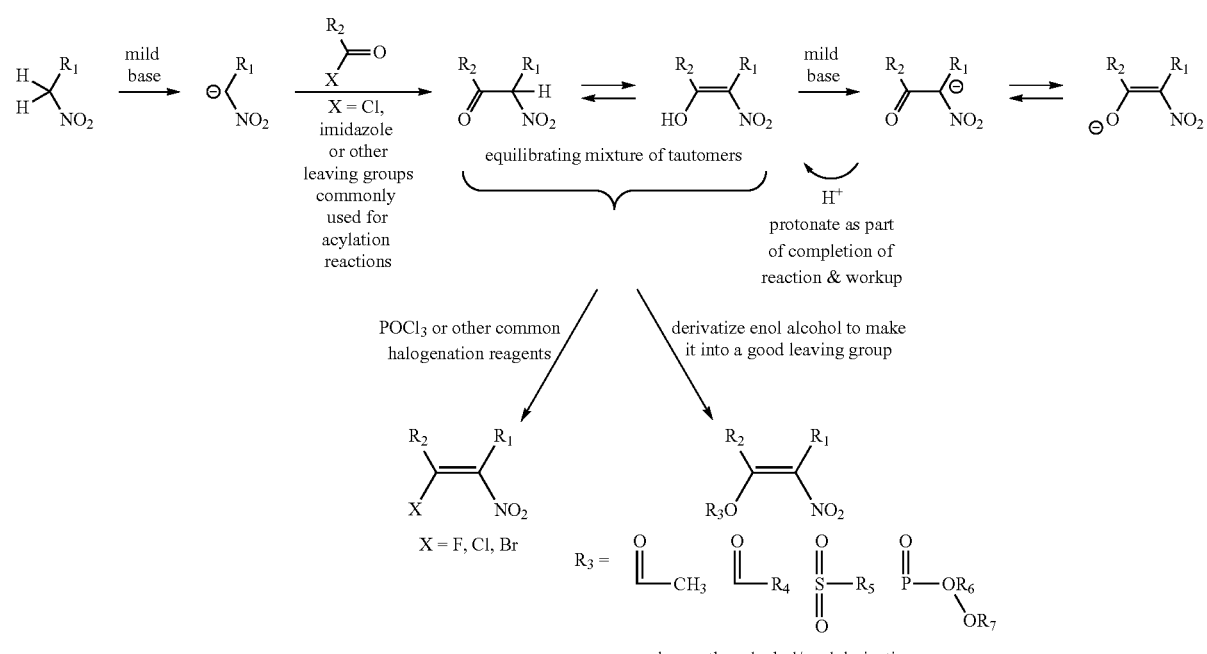

As illustrated, in some embodiments, first component having an electron withdrawing group such as, for example, $NO_2$ as depicted, at a terminus may be treated with a mild base to cause protonation, and this protonated first component may be combined with second component having a carbonyl and a leaving group at its terminus, such as, for example those reagents commonly used in acylation reactions. Reacting the first and second components may result in a mixture of an aliphatic chain with a carbonyl and electron withdrawing group on adjacent carbons of the aliphatic chain and its tautomers as indicated. Various known agents may then be used to replace the carbonyl/-OH with an appropriate leaving group. For example, a halogen leaving group may be added by treating the product of the reaction with a known halogenating agent such as thionyl chloride, $SOCl_2$, phosphorous trichloride, $PCl_3$, or phosphoryl trichloride, $POCl_3$, or the enol alcohol may be derivatized using known methods to create a good leaving such as those described above or illustrated in scheme IV.

attached to the unsaturated or polyunsaturated aliphatic chain, and in other embodiments, an unsaturated aliphatic chain containing a halogen such as, for example, a Cl or Br, end group be combined with a mercaptoalkanoic acid such as, for example, 2-mercaptoacetic acid or 3-mercaptopropionic acid, or an hydroxyalkanoic acid such as, for example, 2-hydroxyacetic acid or 3-hydroxypropionic acid, in an appropriate solvent to produce a thioalkanoic acid or oxyalkanoic acid, covalently attached to the unsaturated or polyunsaturated aliphatic chain. In still other embodiments, a sulfinylalkanoic acid may be prepared by drying a thioalkanoic acid prepared as described above and maintaining the dried product in an oxygen rich environment for a several days. In such embodiments, an electron withdrawing group may be introduced onto the unsaturated or polyunsaturated aliphatic chain by any of the methods provided above either before or after formation of the thioalkanoic acid, oxyalkanoic acid, or sulfinylalkanoic acid.

In certain embodiments, heteroatom containing functionally-enhanced fatty acid inhibitors can be prepared as illustrated in scheme V:

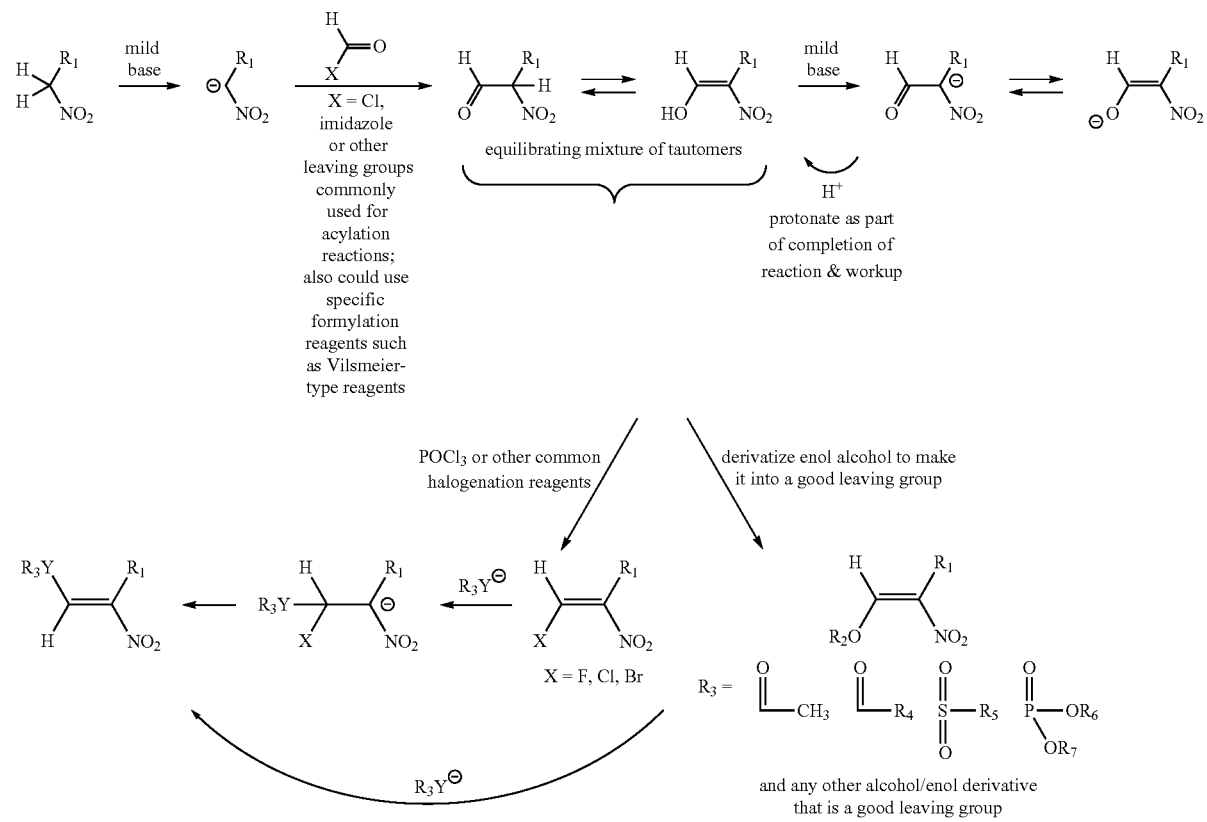

Heteroatom containing fatty acid inhibitors such as those of Group II and Group III fatty acid inhibitors may be prepared using the same methodology as described above for introducing an electron withdrawing group to an unsaturated fatty acid. For example, in some embodiments, an unsaturated aliphatic chain containing toluene sulfonate may be combined with a mercaptoalkanoic acid such as, for example, an 2-mercaptoacetic acid or 3-mercaptopropionic acid, or an hydroxyalkanoic acid such as, for example, 2-hydroxyacetic acid or 3-hydroxypropionic acid, in an appropriate solvent to produce a thioalkanoic acid or oxyalkanoic acid covalently In such embodiments, a leaving group may be added to a first component having electron withdrawing group by reacting the first component with a second component that includes a carbonyl and a leaving group such as, for example, common acylation reagents or, in some embodiments, formulation reagents such as Vilsmeier-type reagents, and reacting the product of this reaction with a halogenating reagent or derivatizing the enol alcohol to form a leaving group. The leaving group containing product of this reaction can then be reacted with a heteroatom containing component, $R_3Y^{-1}$ which can undergo addition at the carbon-carbon double bond to create a Group II functionally-enhanced fatty acid inhibitor.

In other embodiments, heteroatom containing functionally-enhanced fatty acid inhibitors may also be created by the method illustrated in scheme VI:

epoxidation reagent or an aziridination reagent. Thus, treatment with an appropriate epoxidation reagent or an aziridination reagent may allow for formation of a Group IV functionally-enhanced fatty acid inhibitor directly from an activated fatty acid.

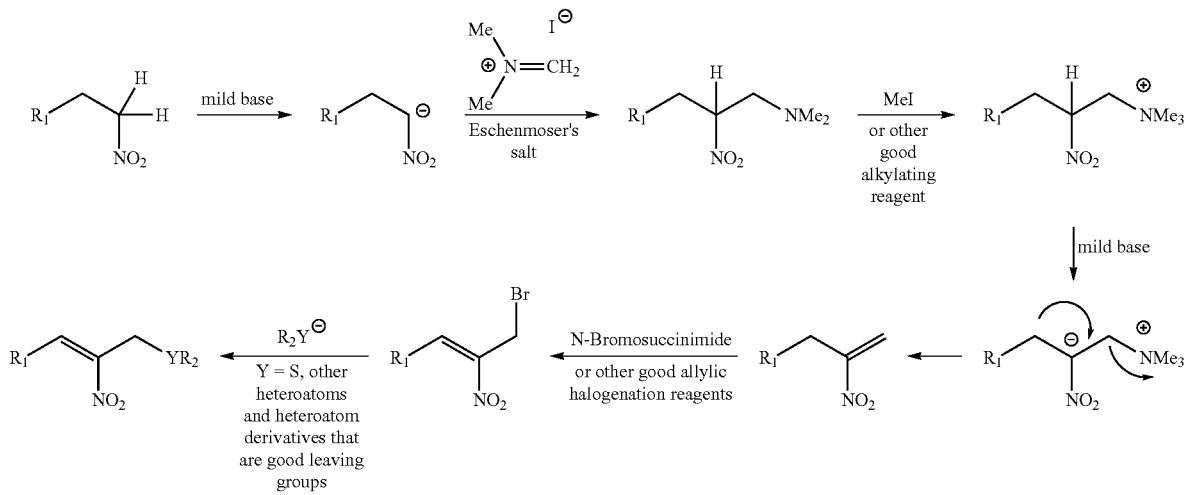

In such embodiments, mild base may be used to deprotonate a first component having an electron withdrawing group, $NO_2$ in this example, and an alkyl of at least 3 carbon atoms, and this deprotonated first component may be reacted with, for example Eschenmoser's salt, $NCH_2(CH_3)_2$, to add a tertiary amine to the first component. This product may than be reacted with an alkylating agent such as, for example, methyl iodide, $CH_3I$, to produce a quaternary amine which can form a carbonyl on the first component in a mild base. An allylic halogenatin agent such as, for example, N-bromosuccinimide, may be used to halogenate the carbonyl thereby providing a leaving group which can be reacted with a heteroatom containing component, $R_3Y^-$, to form a Group III functionally-enhanced fatty acid inhibitor.

Further embodiments are directed to methods for preparing functionally-enhanced fatty acid inhibitors that include a strained heterocylic group such as those of Group IV. For example, in some embodiments, such functionally-enhanced fatty acid inhibitors may be prepared as illustrated in scheme VII:

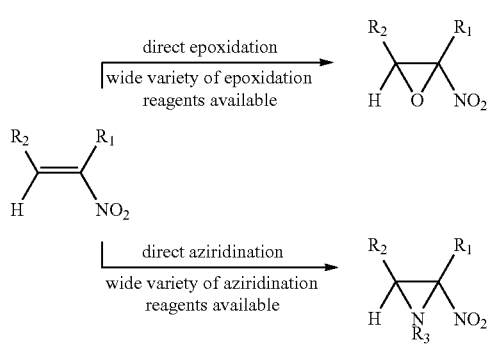

In such embodiments, any activated fatty acid having an electron withdrawing group at a carbon adjacent to a carbon-carbon double bond may be treated with, for example, an In other embodiments, Groups IV functionally-enhanced fatty acid inhibitors may be prepared as illustrated in scheme VIII:

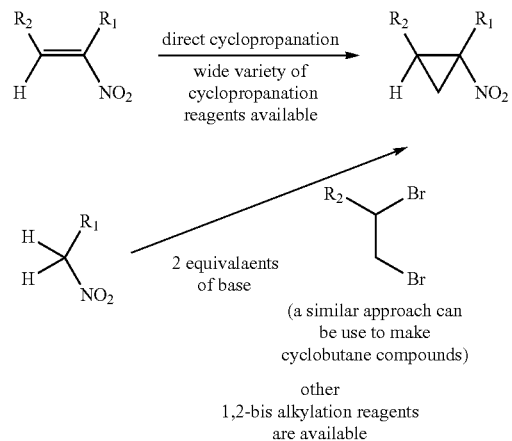

In such embodiments, an activated fatty acid may be treated with a cyclopropanation reagent to create a cyclopropyl containing functionally-enhanced fatty acid inhibitor directly. In other embodiments, a first component may be combined with a base and a 1,2-bis alkylation reagent such as, for example, the 1,2-dibromo alkyl reagent illustrated, to create a cyclopropyl containing Group IV functionally-enhanced fatty acid inhibitor. In embodiments such as those depicted in scheme VIII, R1 can be any length and may contain additional double bonds, functional groups, electron withdrawing groups, heteroatoms, and so on. In still other embodiments, a cyclobutyl containing Group IV functionally-enhanced fatty acid inhibitor can be prepared by combining a first component with a 1,3-bis alkylation reagent, and in still further embodiments, heteroatoms can be provided in the cycloalkyl containing functionally-enhanced fatty acid inhibitors by providing an bis-alkylating reagent that include a heteroatom between leaving groups.

In some embodiments, alkyl chains associated with the fatty acid inhibitors may contain additional functional groups other than double bonds, which may or may not be associated with a carbon-carbon double bond, heteratom, or strained heterocycle either existing before the reaction is carried out. For example, individual $R_1$ and $R_2$ groups shown in Scheme III may include functional groups such as, but not limited to, alkynes, as a part of the chain, with the alkyne in the chain, alcohols, aldehyde carbonyls, ketone carbonyls, derivatives of carbonyl aldehydes and ketones, such as, oximes, hydrazones and any other carbonyl derivative known in the art, amines, amines with other groups known in the art attached to the amine, thiols, thiols with other groups known in the art attached to the thiols, any other functional group known in the art, either as the simple functional group or the functional group with another chain or group attached to it. Such functional groups may be attached to a carbon in the linear or branched chain. Without wishing to be bound by theory, the addition of additional functional groups may alter the targeting and bioavailability of the fatty acid inhibitors of embodiments, such that specific cells or targets it within cells can be targeted.

In yet other embodiments, molecules may contain more than one carbon chain, with two or more carbon chains joined together by a non-carbon group, and in some embodiments, each of the carbon chains can be branched or linear. For example, in certain embodiments, non-carbon functional groups that can join two or more carbon chains together include, but are not limited to, those in the very common functional groups listed below:

Ethers $R_1$—O—$R_2$,
Amines $R_1$—$NR_3$—$R_2$,
Esters $R_1$—C(=O)—O—$R_2$,
Amides $R_1$—C(=O)—$NR_3$—$R_2$
ThioEsters $R_1$—C(=S)—O—$R_2$ or $R_1$—C(=O)—S—$R_2$
ThioAmides $R_1$—C(=S)—$NR_3$—$R_2$ In addition to the common non-carbon multivalent elements found in organics compounds and shown above (oxygen, nitrogen & sulfur), other functional groups known in the art, and based on any other non-carbon multivalent element may be used in embodiments of the invention. In various embodiments, any of the non-carbon chains described above could be incorporated into fatty acid inhibitors using the general synthetic approach shown in III, above, in which the non-carbon chains are in $R_1$, $R_2$ or both.

Pharmaceutical formulations containing the compounds of the invention and a suitable carrier can be in various forms including, but not limited to, solids, solutions, powders, fluid emulsions, fluid suspensions, semi-solids, and dry powders including an effective amount of a fatty acid inhibitor of the invention. It is also known in the art that the active ingredients can be contained in such formulations with pharmaceutically acceptable diluents, fillers, disintegrants, binders, lubricants, surfactants, hydrophobic vehicles, water soluble vehicles, emulsifiers, buffers, humectants, moisturizers, solubilizers, antioxidants, preservatives and the like. The means and methods for administration are known in the art and an artisan can refer to various pharmacologic references for guidance. For example, *Modern Pharmaceutics*, Banker & Rhodes, Marcel Dekker, Inc. (1979); and *Goodman & Gilman's, The Pharmaceutical Basis of Therapeutics,* 6th Edition, MacMillan Publishing Co., New York (1980) both of which are hereby incorporated by reference in their entireties can be consulted.

The compounds of the present invention can be formulated for parenteral or intravenous administration by injection, e.g., by bolus injection or continuous infusion. Formulations for injection can be presented in unit dosage form, e.g., in ampoules or in multi-dose containers, with an added preservative. The compositions can take such forms as suspensions, solutions or emulsions in oily or aqueous vehicles, and can contain formulatory agents such as suspending, stabilizing and/or dispersing agents.

Injectable preparations, for example, sterile injectable aqueous or oleaginous suspensions may be formulated according to the known art using suitable dispersing or wetting agents and suspending agents. The sterile injectable preparation may also be a sterile injectable solution or suspension in a nontoxic parenterally acceptable diluent or solvent, for example, as a solution in 1,3-butanediol. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed including synthetic mono- or diglycerides. In addition, fatty acids diluents such as oleic acid find use in the preparation of injectables. Additional fatty acids diluents that may be useful in embodiments of the invention include, for example, one or more of stearic acid, metallic stearate, sodium stearyl fumarate, fatty acid, fatty alcohol, fatty acid ester, glyceryl behenate, mineral oil, vegetable oil, paraffin, leucine, silica, silicic acid, talc, propylene glycol fatty acid ester, polyethoxylated castor oil, polyethylene glycol, polypropylene glycol, polyalkylene glycol, polyoxyethylene-glycerol fatty ester, polyoxyethylene fatty alcohol ether, polyethoxylated sterol, polyethoxylated castor oil, polyethoxylated vegetable oil, and the like. In some embodiments, the fatty acid diluent may be a mixture of fatty acids. In some embodiments, the fatty acid may be a fatty acid ester, a sugar ester of fatty acid, a glyceride of fatty acid, or an ethoxylated fatty acid ester, and in other embodiments, the fatty acid diluent may be a fatty alcohol such as, for example, stearyl alcohol, lauryl alcohol, palmityl alcohol, palmitolyl acid, cetyl alcohol, capryl alcohol, caprylyl alcohol, oleyl alcohol, linolenyl alcohol, arachidonic alcohol, behenyl alcohol, isobehenyl alcohol, selachyl alcohol, chimyl alcohol, and linoleyl alcohol and the like and mixtures thereof.

Other embodiments of the invention include fatty acid inhibitor prepared as described above which are formulated as a solid dosage form for oral administration including capsules, tablets, pills, powders, and granules. In such embodiments, the active compound may be admixed with one or more inert diluent such as sucrose, lactose, or starch. Such dosage forms may also comprise, as in normal practice, additional substances other than inert diluents, e.g., lubricating agents such as magnesium stearate. In the case of capsules, tablets, and pills, the dosage forms may also comprise buffering agents and can additionally be prepared with enteric coatings.

Preparation of a fatty acid inhibitor in solid dosage form may vary. For example, in one embodiment, a liquid or gelatin formulation of the fatty acid inhibitor may be prepared by combining the fatty acid inhibitor with one or more fatty acid diluent, such as those described above, and adding a thickening agent to the liquid mixture to form a gelatin. The gelatin may then be encapsulated in unit dosage form to form a capsule. In another exemplary embodiment, an oily preparation of a fatty acid inhibitor prepared as described above may be lyophilized to for a solid that may be mixed with one or more pharmaceutically acceptable excipient, carrier or diluent to form a tablet, and in yet another embodiment, the fatty acid inhibitor of an oily preparation may be crystallized to from a solid which may be combined with a pharmaceutically acceptable excipient, carrier or diluent to form a tablet.

Further embodiments which may be useful for oral administration of fatty acid inhibitors include liquid dosage forms. In such embodiments, a liquid dosage may include a pharmaceutically acceptable emulsion, solution, suspension, syrup, and elixir containing inert diluents commonly used in the art, such as water. Such compositions may also comprise adjuvants, such as wetting agents, emulsifying and suspending agents, and sweetening, flavoring, and perfuming agents.

In still further embodiments, fatty acid inhibitors of the invention can be formulated as a depot preparation. Such long acting formulations can be administered by implantation (for example, subcutaneously or intramuscularly) or by intramuscular injection. Depot injections can be administered at about 1 to about 6 months or longer intervals. Thus, for example, the compounds can be formulated with suitable polymeric or hydrophobic materials (for example, as an emulsion in an acceptable oil) or ion exchange resins, or as sparingly soluble derivatives, for example, as a sparingly soluble salt.

Other suitable diluents for injectable formulations include, but are not limited to those described below:

Vegetable oil: As used herein, the term "vegetable oil" refers to a compound, or mixture of compounds, formed from ethoxylation of vegetable oil, wherein at least one chain of polyethylene glycol is covalently bound to the vegetable oil. In some embodiments, the fatty acids has between about twelve carbons to about eighteen carbons. In some embodiments, the amount of ethoxylation can vary from about 2 to about 200, about 5 to 100, about 10 to about 80, about 20 to about 60, or about 12 to about 18 of ethylene glycol repeat units. The vegetable oil may be hydrogenated or unhydrogenated. Suitable vegetable oils include, but are not limited to castor oil, hydrogenated castor oil, sesame oil, corn oil, peanut oil, olive oil, sunflower oil, safflower oil, soybean oil, benzyl benzoate, sesame oil, cottonseed oil, and palm oil. Other suitable vegetable oils include commercially available synthetic oils such as, but not limited to, Miglyol™ 810 and 812 (available from Dynamit Nobel Chemicals, Sweden) Neobee™ M5 (available from Drew Chemical Corp.), Alofine™ (available from Jarchem Industries), the Lubritab™ series (available from JRS Pharma), the Sterotex™ (available from Abitec Corp.), Softisan™ 154 (available from Sasol), Croduret™ (available from Croda), Fancol™ (available from the Fanning Corp.), Cutina™ HR (available from Cognis), Simulsol™ (available from CJ Petrow), EmCon™ CO (available from Amisol Co.), Lipvol™ CO, SES, and HS-K (available from Lipo), and Sterotex™ HM (available from Abitec Corp.). Other suitable vegetable oils, including sesame, castor, corn, and cottonseed oils, include those listed in R. C. Rowe and P. J. Shesky, *Handbook of Pharmaceutical Excipients*, (2006), 5th ed., which is incorporated herein by reference in its entirety. Suitable polyethoxylated vegetable oils, include but are not limited to, Cremaphor™ EL or RH series (available from BASF), Emulphor™ EL-719 (available from Stepan products), and Emulphor™ EL-620P (available from GAF).

Mineral oils: As used herein, the term "mineral oil" refers to both unrefined and refined (light) mineral oil. Suitable mineral oils include, but are not limited to, the Avatech™ grades (available from Avatar Corp.), Drakeol™ grades (available from Penreco), Sirius™ grades (available from Shell), and the Citation™ grades (available from Avater Corp.).

Castor oils: As used herein, the term "castor oil", refers to a compound formed from the ethoxylation of castor oil, wherein at least one chain of polyethylene glycol is covalently bound to the castor oil. The castor oil may be hydrogenated or unhydrogenated. Synonyms for polyethoxylated castor oil include, but are not limited to polyoxyl castor oil, hydrogenated polyoxyl castor oil, mcrogolglyceroli ricinoleas, macrogolglyceroli hydroxystearas, polyoxyl 35 castor oil, and polyoxyl 40 hydrogenated castor oil. Suitable polyethoxylated castor oils include, but are not limited to, the Nikkol™ HCO series (available from Nikko Chemicals Co. Ltd.), such as Nikkol HCO-30, HC-40, HC-50, and HC-60 (polyethylene glycol-30 hydrogenated castor oil, polyethylene glycol-40 hydrogenated castor oil, polyethylene glycol-50 hydrogenated castor oil, and polyethylene glycol-60 hydrogenated castor oil, Emulphor™ EL-719 (castor oil 40 mole-ethoxylate, available from Stepan Products), the Cremophore™ series (available from BASF), which includes Cremophore RH40, RH60, and EL35 (polyethylene glycol-40 hydrogenated castor oil, polyethylene glycol-60 hydrogenated castor oil, and polyethylene glycol-35 hydrogenated castor oil, respectively), and the Emulgin® RO and HRE series (available from Cognis PharmaLine). Other suitable polyoxyethylene castor oil derivatives include those listed in R. C. Rowe and P. J. Shesky, *Handbook of Pharmaceutical Excipients*, (2006), 5th ed., which is incorporated herein by reference in its entirety.

Sterol: As used herein, the term "sterol" refers to a compound, or mixture of compounds, derived from the ethoxylation of sterol molecule. Suitable polyethoyxlated sterols include, but are not limited to, PEG-24 cholesterol ether, Solulan™ C-24 (available from Amerchol); PEG-30 cholestanol, Nikkol™ DHC (available from Nikko); Phytosterol, GENEROL™ series (available from Henkel); PEG-25 phyto sterol, Nikkol™ BPSH-25 (available from Nikko); PEG-5 soya sterol, Nikkol™ BPS-5 (available from Nikko); PEG-10 soya sterol, Nikkol™ BPS-10 (available from Nikko); PEG-20 soya sterol, Nikkol™ BPS-20 (available from Nikko); and PEG-30 soya sterol, Nikkol™ BPS-30 (available from Nikko). As used herein, the term "PEG" refers to polyethylene glycol.

Polyethylene glycol: As used herein, the term "polyethylene glycol" or "PEG" refers to a polymer containing ethylene glycol monomer units of formula —O—$CH_2$—$CH_2$—. Suitable polyethylene glycols may have a free hydroxyl group at each end of the polymer molecule, or may have one or more hydroxyl groups etherified with a lower alkyl, e.g., a methyl group. Also suitable are derivatives of polyethylene glycols having esterifiable carboxy groups. Polyethylene glycols useful in the present invention can be polymers of any chain length or molecular weight, and can include branching. In some embodiments, the average molecular weight of the polyethylene glycol is from about 200 to about 9000. In some embodiments, the average molecular weight of the polyethylene glycol is from about 200 to about 5000. In some embodiments, the average molecular weight of the polyethylene glycol is from about 200 to about 900. In some embodiments, the average molecular weight of the polyethylene glycol is about 400. Suitable polyethylene glycols include, but are not limited to polyethylene glycol-200, polyethylene glycol-300, polyethylene glycol-400, polyethylene glycol-600, and polyethylene glycol-900. The number following the dash in the name refers to the average molecular weight of the polymer. In some embodiments, the polyethylene glycol is polyethylene glycol-400. Suitable polyethylene glycols include, but are not limited to the Carbowax™ and Carbowax™ Sentry series (available from Dow), the Lipoxol™ series (available from Brenntag), the Lutrol™ series (available from BASF), and the Pluriol™ series (available from BASF).

Propylene glycol fatty acid ester: As used herein, the term "propylene glycol fatty acid ester" refers to an monoether or diester, or mixtures thereof, formed between propylene glycol or polypropylene glycol and a fatty acid. Fatty acids that are useful for deriving propylene glycol fatty alcohol ethers include, but are not limited to, those defined herein. In some embodiments, the monoester or diester is derived from propylene glycol. In some embodiments, the monoester or diester has about 1 to about 200 oxypropylene units. In some embodiments, the polypropylene glycol portion of the molecule has about 2 to about 100 oxypropylene units. In some embodiments, the monoester or diester has about 4 to about 50 oxypropylene units. In some embodiments, the monoester or diester has about 4 to about 30 oxypropylene units. Suitable propylene glycol fatty acid esters include, but are not limited to, propylene glycol laurates: Lauroglycol™ FCC and 90 (available from Gattefosse); propylene glycol caprylates: Capryol™ PGMC and 90 (available from Gatefosse); and propylene glycol dicaprylocaprates: Labrafac™ PG (available from Gatefosse).

Stearoyl macrogol glyceride: Stearoyl macrogol glyceride refers to a polyglycolized glyceride synthesized predominately from stearic acid or from compounds derived predominately from stearic acid, although other fatty acids or compounds derived from other fatty acids may used in the synthesis as well. Suitable stearoyl macrogol glycerides include, but are not limited to, Gelucire® 50/13 (available from Gattefosse).

In some embodiments, the diluent component comprises one or more of mannitol, lactose, sucrose, maltodextrin, sorbitol, xylitol, powdered cellulose, microcrystalline cellulose, carboxymethylcellulose, carboxyethylcellulose, methylcellulose, ethylcellulose, hydroxyethylcellulose, methylhydroxyethylcellulose, starch, sodium starch glycolate, pregelatinized starch, a calcium phosphate, a metal carbonate, a metal oxide, or a metal aluminosilicate.

Exemplary excipients or carriers for use in solid and/or liquid dosage forms include, but are not limited to:

Sorbitol: Suitable sorbitols include, but are not limited to, PharmSorbidex E420 (available from Cargill), Liponic 70-NC and 76-NC (available from Lipo Chemical), Neosorb (available from Roquette), Partech SI (available from Merck), and Sorbogem (available from SPI Polyols).

Starch, sodium starch glycolate, and pregelatinized starch include, but are not limited to, those described in R. C. Rowe and P. J. Shesky, *Handbook of Pharmaceutical Excipients*, (2006), 5th ed., which is incorporated herein by reference in its entirety.

Disintegrant: The disintegrant may include one or more of croscarmellose sodium, carmellose calcium, crospovidone, alginic acid, sodium alginate, potassium alginate, calcium alginate, an ion exchange resin, an effervescent system based on food acids and an alkaline carbonate component, clay, talc, starch, pregelatinized starch, sodium starch glycolate, cellulose floc, carboxymethylcellulose, hydroxypropylcellulose, calcium silicate, a metal carbonate, sodium bicarbonate, calcium citrate, or calcium phosphate.

Still further embodiments of the invention include fatty acid inhibitors administered in combination with other active such as, for example, adjuvants, protease inhibitors, or other compatible drugs or compounds where such combination is seen to be desirable or advantageous in achieving the desired effects of the methods described herein.

What is claimed is:

1. A compound represented the formula:

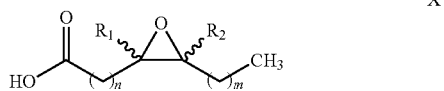

or pharmaceutically acceptable salt thereof, wherein:
$R_1$ is nitro(—$NO_2$);
$R_2$ is H; and
m is 7 and n is 7.

2. A composition comprising compound of claim 1, and a pharmaceutically acceptable carrier, excipient, or combination thereof.

3. The composition of claim 2, further comprising one or more of diluents, fillers, disintegrants, binders, lubricants, surfactants, hydrophobic vehicles, water soluble vehicles, emulsifiers, buffers, humectants, moisturizers, solubilizers, antioxidants, preservatives or combinations thereof.

* * * * *